(12) United States Patent
Wilson

(10) Patent No.: US 9,943,563 B2
(45) Date of Patent: Apr. 17, 2018

(54) COMPOSITIONS AND METHODS FOR TREATING VITILIGO

(71) Applicant: Stealth Peptides International, Inc., Monaco (MC)

(72) Inventor: D. Travis Wilson, Newton, MA (US)

(73) Assignee: STEALTH BIOTHERAPEUTICS CORP, Monaco (MC)

( * ) Notice: Subject to any disclaimer, the term of this patent is extended or adjusted under 35 U.S.C. 154(b) by 0 days.

(21) Appl. No.: 15/100,926

(22) PCT Filed: Dec. 2, 2014

(86) PCT No.: PCT/US2014/068212
§ 371 (c)(1),
(2) Date: Jun. 1, 2016

(87) PCT Pub. No.: WO2015/084875
PCT Pub. Date: Jun. 11, 2015

(65) Prior Publication Data
US 2016/0296589 A1 Oct. 13, 2016

Related U.S. Application Data

(60) Provisional application No. 61/910,742, filed on Dec. 2, 2013.

(51) Int. Cl.
*A61K 38/07* (2006.01)
*G01N 33/68* (2006.01)
*G01N 33/50* (2006.01)

(52) U.S. Cl.
CPC ......... *A61K 38/07* (2013.01); *G01N 33/5044* (2013.01); *G01N 33/5091* (2013.01); *G01N 33/6893* (2013.01); *G01N 2800/207* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,522,811 | A | 6/1985 | Eppstein et al. |
| 4,708,934 | A | 11/1987 | Gilligan et al. |
| 4,757,019 | A | 7/1988 | Eisinger et al. |
| 5,674,534 | A | 10/1997 | Zale et al. |
| 5,716,644 | A | 2/1998 | Zale et al. |
| 6,468,798 | B1 | 10/2002 | Debs et al. |
| 2011/0039766 | A1 | 2/2011 | Szeto |
| 2012/0021029 | A1 | 1/2012 | Garcia Sanz et al. |
| 2013/0316942 | A1 | 11/2013 | Mograbi et al. |

FOREIGN PATENT DOCUMENTS

| | | |
|---|---|---|
| EP | 0 308 067 | 3/1989 |
| EP | 0 382 403 | 8/1990 |
| WO | WO-96/40073 | 12/1996 |
| WO | WO-99/15154 | 4/1999 |
| WO | WO-00/38651 | 7/2000 |
| WO | WO-2013/126775 | 8/2013 |
| WO | WO-2014/165607 | 10/2014 |

OTHER PUBLICATIONS

Matin, "Vitiligo in adults and children", Clinical Evidence, 2011, pp. 1-27.*
Lewis, "Vitiligo: More than a Cosmetic Issue", Vitiligo Support. com, 2006, pp. 1-6.*
Vitiligo, Clinuvel Pharmaceuticals, pp. 1-16; http://clinuvel.com/scienceofskin/; accessed Apr. 13, 2017.*
"Prevent." Merriam-Webster.com. Merriam-Webster, n.d. Web. Apr. 13, 2017; p. 1.*
Amselem, S., "Liposome Technology," (1993), vol. 1, 2nd Ed. CRC Press, (26 pages).
Harris, John E. et al., "A Mouse Model of Vitiligo with Focused Epidermal Depigmentation Requires IFN-γ for Autoreactive CD8+ T-Cell Accumulation in the Skin," J of Investigative Dermatology, (Jul. 2012), vol. 132, Issue 7, pp. 1869-1876.
International Search Report and Written Opinion of the International Searching Authority for Application No. PCT/US2014/068212 dated Mar. 17, 2015, 9 pages.
Kozarich, John W. et al., "Next generation therapeutics: Looking to the horizon: Editorial overview," Current Opinion in Chemical Biology, (1998), vol. 2, Issue 4, pp. 439-440.
Kumar, Ravinder et al., "Development of melanocyte-keratinocyte co-culture model for controls and vitiligo to assess regulators of pigmentation and melanocytes," Indian J of Dermatology Venereology and Leprology, (Oct. 1, 2012), vol. 78, Issue 5, pp. 599-604.
Lerner, Aaron B. et al., "A mouse model for vitiligo," J of Investigative Dermatology, (Sep. 1986), vol. 87, Issue 3, pp. 299-304.
Lichtenberg, Dov et al., "Liposomes: Preparation, Characterization, and Preservation," Methods Biochem. Anal., (1998), vol. 33, pp. 337-462.
Mizuguchi, Hiroyuki et al., "Intratumor administration of fusogenic liposomes containing fragment A of diphtheria toxin suppresses tumor growth," Cancer Lett., (1996), vol. 100, Issue 1, pp. 63-69.
Ray, Martha V.L. et al., "Production of Recombinant Salmon Calcitonin by In Vitro Amidation of an *Escherichia coli* Produced Precursor Peptide," Nature Biotechnology, (1993), vol. 11, Issue 1, pp. 64-70.

(Continued)

*Primary Examiner* — Lianko G Garyu
(74) *Attorney, Agent, or Firm* — Foley & Lardner LLP

(57) ABSTRACT

The present technology provides methods of preventing or treating vitiligo. The methods provide administering aromatic-cationic peptides in effective amounts to treat or ameliorate melanocyte degeneration such as that found in a subject suffering from, or predisposed to vitiligo. In some embodiments, the methods comprise administering to a subject suffering from, or at risk for vitiligo, an effective amount of an aromatic-cationic peptide to subjects in need thereof. The present technology relates to the treatment, amelioration or prevention of vitiligo in mammals or mammalian cells, through administration of therapeutically effective amounts of aromatic-cationic peptides, such as D-Arg-2',6'-Dmt-Lys-Phe-NH2.

8 Claims, 2 Drawing Sheets

(56) References Cited

OTHER PUBLICATIONS

Reddy, K. Rajender, "Controlled-Release, Pegylation, Liposomal Formulations: New Mechanisms in the Delivery of Injectable Drugs," Ann Pharmacother., (Jul./Aug. 2000), vol. 34, pp. 915-923.
Van Den Boorn, Jasper G. et al., "Autoimmune Destruction of Skin Melanocytes by Perilesional T Cells from Vitiligo Patients," J of Investigative Dermatology, (2009), vol. 129, pp. 2220-2232.
Weiner, Alan L., "Liposomes for Protein Delivery: Selecting Manufacture and Development Processes," Immunomethods, (1994), 4(3), pp. 201-209.
Yang, Fan et al., "Effects of 4-Tertiary Butylphenol on the Tyrosinase Activity in Human Melanocytes," Pigment Cell Res, (1999), vol. 12, Issue 4, pp. 237-245.
Search Report issued on European Application 14866993.0, dated Jun. 16, 2017.

* cited by examiner

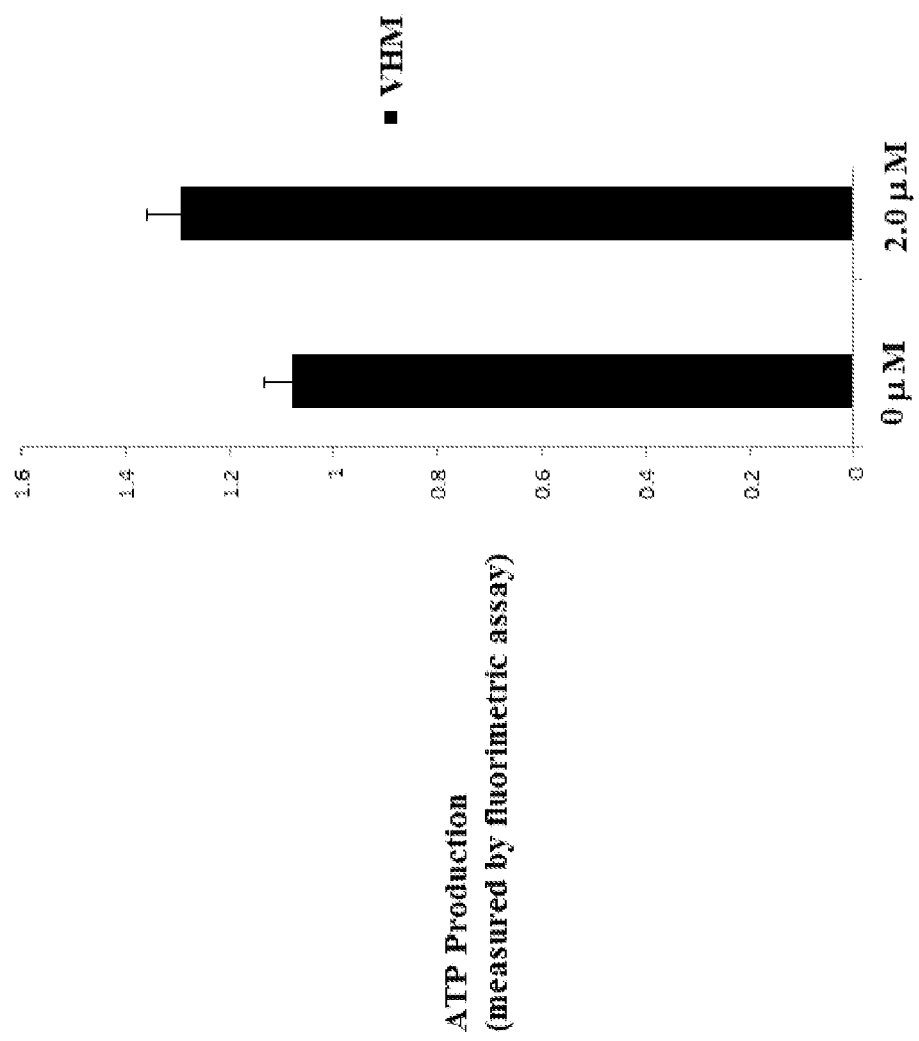

SEQUENCE LISTING

<160> NUMBER OF SEQ ID NOS: 20

<210> SEQ ID NO 1
<211> LENGTH: 8
<212> TYPE: PRT

-continued

```
<213> ORGANISM: Artificial Sequence
<220> FEATURE:
<223> OTHER INFORMATION: Description of Artificial Sequence: Synthetic
      peptide

<400> SEQUENCE: 1

Tyr Arg Phe Lys Glu His Trp Arg
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Gln Tyr Arg Phe Trp
1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Dimethyltyrosine

<400> SEQUENCE: 3

Arg Arg Tyr Phe
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dimethyltyrosine

<400> SEQUENCE: 4

Arg Tyr Lys Phe
1

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dimethyltyrosine

<400> SEQUENCE: 5

Arg Tyr Lys Phe Cys
1               5
```

```
<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dimethyltyrosine

<400> SEQUENCE: 6

Arg Tyr Phe Lys
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Dimethyltyrosine

<400> SEQUENCE: 7

Arg Lys Tyr Phe
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dimethyltyrosine

<400> SEQUENCE: 8

Arg Lys Phe Tyr
1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Dimethyltyrosine

<400> SEQUENCE: 9

Arg Phe Tyr Lys
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 10

Arg Tyr Lys Phe
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dimethyltyrosine

<400> SEQUENCE: 11

Tyr Phe Arg Lys
1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dimethyltyrosine

<400> SEQUENCE: 12

Arg Tyr Lys Phe
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dimethyltyrosine

<400> SEQUENCE: 13

His Tyr Lys Phe
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dimethyltyrosine

<400> SEQUENCE: 14

Lys Tyr Lys Phe
1

```
<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Arg Phe Lys
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dimethyltyrosine

<400> SEQUENCE: 16

Lys Phe Arg Tyr
1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Dimethyltyrosine

<400> SEQUENCE: 17

Phe Arg Tyr Lys
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Arg Phe Lys
1

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Phe Arg Phe Lys Glu Cys Gly
1               5

<210> SEQ ID NO 20
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dimethyltyrosine

<400> SEQUENCE: 20

Phe Tyr Arg Lys
1
```

COMPOSITIONS AND METHODS FOR TREATING VITILIGO

CROSS-REFERENCE TO RELATED APPLICATIONS

This application is a U.S. national phase application under 35 U.S.C. § 371 of International Application No. PCT/US2014/068212, filed on Dec. 2, 2014, which claims the benefit of and priority to U.S. Application No. 61/910,742 filed on Dec. 2, 2013, the contents of each are incorporated by reference herein in their entireties.

SEQUENCE LISTING

The instant application contains a Sequence Listing which has been submitted electronically in ASCII format and is hereby incorporated by reference in its entirety. Said ASCII copy, created on May 15, 2017, is named 091151-0932_SL.txt and is 5,054 bytes in size.

TECHNICAL FIELD

The present technology relates generally to compositions and methods of preventing or treating vitiligo. In particular, embodiments of the present technology relate to administering aromatic-cationic peptides in effective amounts to treat or ameliorate the degeneration of melanocytes such as that found in a subject suffering from, or predisposed to vitiligo.

BACKGROUND

The following description is provided to assist the understanding of the reader. None of the information provided or references cited is admitted to be prior art.

Vitiligo is a pigmentation disorder in which melanocytes, the cells responsible for skin pigmentation, are destroyed. As a result, white patches appear on the skin in different parts of the body. Although patches are initially small, they often enlarge and change shape. Vitiligo lesions can appear anywhere, but are most commonly found on the acral areas, mucous membranes (tissues that line the inside of the mouth and nose), retina and genitals. Other symptoms include increased photosensitivity, decreased contact sensitivity response to dinitrochlorobenzene, and premature whitening or graying of hair that grows on areas affected by vitiligo. A Black light can be used in the early phase of this disease for identification and to determine effectiveness of treatment. Skin with vitiligo, when exposed to a Black light, will glow yellow, green or blue, in contrast to healthy skin which will have no reaction.

A number of medical therapies including topical steroid therapy, psoralen photochemotherapy, and depigmentation can reduce the appearance of vitiligo. However, each of these therapies is associated with drawbacks in efficacy and/or severe side effects such as skin shrinkage, severe sunburn, blistering, hyperpigmentation, cataracts, inflammation, nausea, vomiting, itching, abnormal hair growth, and skin cancer. Furthermore, surgical therapies are not optimal because they are only appropriate for a subset of vitiligo patients and are accompanied by the risk of infection, scarring, blistering, and abnormal pigmentation. Thus the need for therapeutic strategies that effectively and safely combat vitiligo still remains.

SUMMARY OF THE PRESENT TECHNOLOGY

The present technology relates to the treatment, amelioration or prevention of vitiligo in mammals or mammalian cells, through administration of therapeutically effective amounts of aromatic-cationic peptides, such as D-Arg-2',6'-Dmt-Lys-Phe-NH$_2$, or pharmaceutically acceptable salts thereof, such as acetate salt, tartrate salt, or trifluoroacetate salt, to subjects in need thereof. In some aspects, the present technology relates to treating, ameliorating or preventing the degeneration of melanocytes in a subject, or in mammalian cells in need thereof, by administering aromatic-cationic peptides as disclosed herein. In some embodiments, the mammalian subject is at risk for, or suffering from, or at increased risk for vitiligo. In some embodiments, the subject is suffering from or is at increased risk of a disease or conditions characterized by a gene mutation which affects melanocyte survival. In some embodiments, the subject is suffering from or is predisposed to a disease or condition characterized by a mutation in NLRP1. In some embodiments, the subject is suffering from or is predisposed to a disease or condition characterized by a mutation in TYR. In some embodiments, the degeneration of melanocytes is associated with at least one gene mutation. In some embodiments, the gene mutation includes a mutation in one or more of the following genes, or genetic regions: NLRP1, TYR, HLA class I, HLA class II, HLA class III, PTPN22, XBP1, IL2RA, LPP, RERE, FOXP1, TSLP, CCR6, GZMB, UBASH3A, C1QTNF6, FOXP3.

In some embodiments, the mammalian cell is either in situ, ex vivo or in vivo. In some embodiments, melanocyte degeneration is due to abnormalities in a biochemical or metabolic pathway. In some embodiments, melanocyte degeneration is due to abnormalities in the metabolism of biopterins, phenols, or catechols. In some embodiments, melanocyte degeneration is due to stress caused by exposure to phenolic/catecholic derivatives, such as 4-tertiary butyl phenol. In some embodiments, melanocyte degeneration is due to an autoimmune response.

Also disclosed herein are methods for treating vitiligo in a subject in need thereof, the method comprising: administering a therapeutically effective amount of an aromatic-cationic peptide, such as D-Arg-2',6'-Dmt-Lys-Phe-NH$_2$ or a pharmaceutically acceptable salt thereof, thereby treating or ameliorating at least one symptom of vitiligo.

In some embodiments of the disclosed methods, the symptoms of vitiligo may include any one or more of the following: increased photosensitivity, decreased contact sensitivity response to dinitrochlorobenzene, depigmentation of the skin, mucous membranes (tissues that line the inside of the mouth and nose), retina, or genitals, and premature whitening or graying of hair on the scalp, eyelashes, eyebrows or beard.

In some embodiments of the disclosed methods, vitiligo may be associated with one or more of the following: melanoma, autoimmune thyroid disease (Hashimoto's thyroiditis and Graves' disease), pernicious anemia, rheumatoid arthritis, psoriasis, type I diabetes, Addison's disease, celiac disease, inflammatory bowel disorder, and systemic lupus erythematosus.

In some embodiments of the disclosed methods, vitiligo is associated with at least one gene mutation. In some embodiments of the disclosed methods, the gene mutation is located in one or more of the following genes or genetic regions: NLRP1, TYR, HLA class I, HLA class II, HLA class III, PTPN22, XBP1, IL2RA, LPP, RERE, FOXP1, TSLP, CCR6, GZMB, UBASH3A, C1QTNF6, FOXP3.

In some aspects, methods for treating, preventing or ameliorating melanocyte degeneration and depigmentation are provided. In some embodiments, the methods include: contacting the cell with a therapeutically effective amount of an aromatic-cationic peptide, such as D-Arg-2',6'-Dmt-Lys-Phe-NH$_2$ or a pharmaceutically acceptable salt thereof, thereby treating, preventing or ameliorating melanocyte degeneration and depigmentation. In some embodiments, the cell is a mammalian cell. In some embodiments, the cell is in a mammalian subject.

In some aspects, methods for treating, preventing or ameliorating melanocyte degeneration and depigmentation induced by exposure to 4-tertiary butyl phenol are provided. In some embodiments, the methods include: contacting the cell with a therapeutically effective amount of an aromatic-cationic peptide, such as D-Arg-2',6'-Dmt-Lys-Phe-NH$_2$ or a pharmaceutically acceptable salt thereof, thereby treating, preventing or ameliorating melanocyte degeneration and depigmentation induced by exposure to 4-tertiary butyl phenol.

In some aspects, methods for treating, preventing or ameliorating melanocyte degeneration and depigmentation by reducing T-cell accumulation and cytotoxic activity in epidermal cells are provided. In some embodiments, the methods include: contacting the cell with a therapeutically effective amount of an aromatic-cationic peptide, such as D-Arg-2',6'-Dmt-Lys-Phe-NH$_2$ or a pharmaceutically acceptable salt thereof, thereby treating, preventing or ameliorating melanocyte degeneration and depigmentation by reducing T-cell accumulation and cytotoxic activity in the epidermal cell. In some embodiments, the cell is a mammalian cell. In some embodiments, the cell is in a mammalian subject.

In some aspects, the disclosure provides methods for the treatment or prevention of vitiligo, comprising administering to a subject in need thereof a therapeutically effective amount of an aromatic-cationic peptide or a pharmaceutically acceptable salt thereof, e.g., D-Arg-2',6'-Dmt-Lys-Phe-NH$_2$, or pharmaceutically acceptable salts thereof, such as acetate salt, tartrate salt, or trifluoroacetate salt. In some embodiments, the method further comprises administration of one or more additional therapeutic agents. In some embodiments, the aromatic-cationic peptide is a peptide having:
- at least one net positive charge;
- a minimum of four amino acids;
- a maximum of about twenty amino acids;
- a relationship between the minimum number of net positive charges ($p_m$) and the total number of amino acid residues (r) wherein $3p_m$ is the largest number that is less than or equal to r+1; and a relationship between the minimum number of aromatic groups (a) and the total number of net positive charges ($p_t$) wherein $2a$ is the largest number that is less than or equal to $p_t+1$, except that when a is 1, $p_t$ may also be 1. In particular embodiments, the subject is a human.

In some embodiments, $2p_m$ is the largest number that is less than or equal to r+1, and a may be equal to $p_t$. The aromatic-cationic peptide may be a water-soluble peptide having a minimum of two or a minimum of three positive charges. In some embodiments, the peptide comprises one or more non-naturally occurring amino acids, for example, one or more D-amino acids. In some embodiments, the C-terminal carboxyl group of the amino acid at the C-terminus is amidated. In certain embodiments, the peptide has a minimum of four amino acids. The peptide may have a maximum of about 6, a maximum of about 9, or a maximum of about 12 amino acids.

In some embodiments, the peptide comprises a tyrosine or a 2',6'-dimethyltyrosine (Dmt) residue at the N-terminus. For example, the peptide may have the formula Tyr-D-Arg-Phe-Lys-NH$_2$ or 2',6'-Dmt-D-Arg-Phe-Lys-NH$_2$. In another embodiment, the peptide comprises a phenylalanine or a 2',6'-dimethylphenylalanine residue at the N-terminus. For example, the peptide may have the formula Phe-D-Arg-Phe-Lys-NH$_2$ or 2',6'-Dmp-D-Arg-Phe-Lys-NH$_2$. In a particular embodiment, the aromatic-cationic peptide has the formula D-Arg-2',6'-Dmt-Lys-Phe-NH$_2$ or a pharmaceutically acceptable salt thereof such as acetate salt, tartrate salt, or trifluoroacetate salt.

In one embodiment, the peptide is defined by formula I:

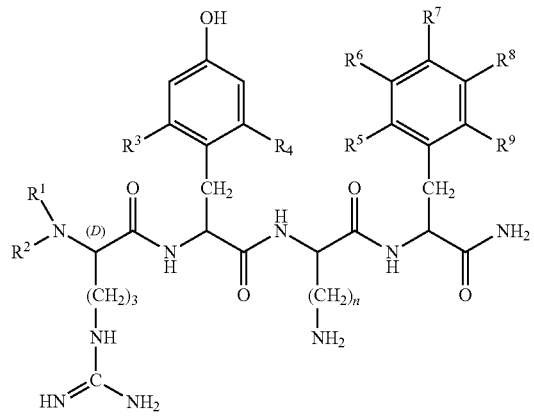

wherein $R^1$ and $R^2$ are each independently selected from
(i) hydrogen;
(ii) linear or branched $C_1$-$C_6$ alkyl;

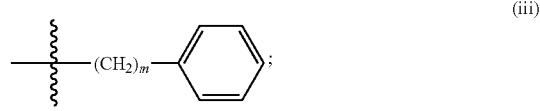

(iii)

(iv)

(v)

where m = 1-3

$R^3$ and $R^4$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo;

$R^5$, $R^6$, $R^7$, $R^8$, and $R^9$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;

(vi) $C_1$-$C_4$ dialkylamino;
(vii) nitro;
(viii) hydroxyl;
(ix) halogen, where "halogen" encompasses chloro, fluoro, bromo, and iodo; and n is an integer from 1 to 5.

In a particular embodiment, $R^1$ and $R^2$ are hydrogen; $R^3$ and $R^4$ are methyl; $R^5$, $R^6$, $R^7$, $R^8$, and $R^9$ are all hydrogen; and n is 4.

In one embodiment, the peptide is defined by formula II:

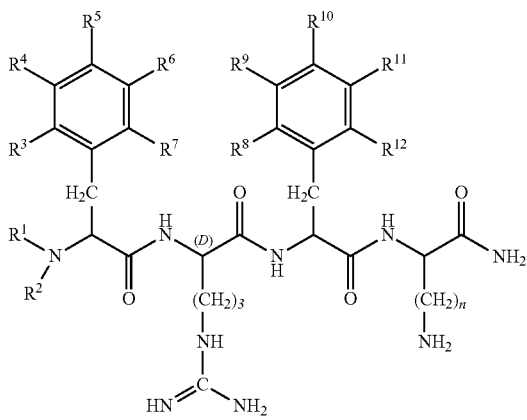

wherein $R^1$ and $R^2$ are each independently selected from
(i) hydrogen;
(ii) linear or branched $C_1$-$C_6$ alkyl;

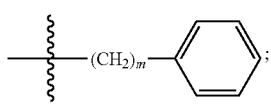 (iii)

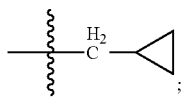 (iv)

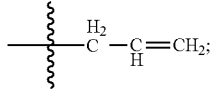 (v)

where m = 1-3

$R^3$, $R^4$, $R^5$, $R^6$, $R^7$, $R^8$, $R^9$, $R^{10}$, $R^{11}$ and $R^{12}$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and n is an integer from 1 to 5.

In a particular embodiment, $R^1$, $R^2$, $R^3$, $R^4$, $R^5$, $R^6$, $R^7$, $R^8$, $R^9$, $R^{10}$, $R^{11}$, and $R^{12}$ are all hydrogen; and n is 4. In another embodiment, $R^1$, $R^2$, $R^3$, $R^4$, $R^5$, $R^6$, $R^7$, $R^8$, $R^9$, and $R^{11}$ are all hydrogen; $R^8$ and $R^{12}$ are methyl; $R^{10}$ is hydroxyl; and n is 4.

The aromatic-cationic peptides may be administered in a variety of ways. In some embodiments, the peptides may be administered orally, topically, intranasally, intraperitoneally, intravenously, subcutaneously, or transdermally (e.g., by iontophoresis). In some embodiments, the aromatic-cationic peptide is administered by an intracoronary route or an intra-arterial route.

In one embodiment, the present technology provides methods for the treatment, amelioration or prevention of vitiligo in a mammalian subject in need thereof, and/or treating or ameliorating the degeneration of melanocytes in a subject in need thereof, by administering aromatic-cationic peptides as disclosed herein, the method comprising administering to the subject a therapeutically effective amount of an aromatic-cationic peptide, such as D-Arg-2',6'-Dmt-Lys-Phe-NH$_2$ or a pharmaceutically acceptable salt thereof, such as acetate salt, tartrate salt, or trifluoroacetate salt, thereby preventing or treating vitiligo and/or signs or symptoms thereof. In one embodiment, the method further comprises the step administering one or more additional therapeutic agents to the subject. In one embodiment, the mammalian subject is at risk for, or suffering from, or is at increased risk for vitiligo. In some embodiments, the subject is suffering from or is at increased risk for a disease or condition characterized by melanocyte degeneration. In some embodiments, the subject is suffering from or is at increased risk for a disease or condition characterized by a genetic mutation which affects melanocyte survival. In some embodiments, the subject is suffering from or is at increased risk for a disease or condition characterized by a mutation in NLRP1. In some embodiments, the subject is suffering from or is at increased risk for a disease or condition characterized by a mutation in TYR. In some embodiments, the subject is treated by administering an aromatic-cationic peptide as disclosed herein.

In another aspect, the present technology provides a diagnostic assay for identifying a subject for treatment with one or more aromatic-cationic peptides, wherein the assay includes: removing tissue from the subject, wherein the tissue exhibits the phenotype or symptoms of vitiligo; isolating the melanocytes from the tissue; culturing the isolated melanocytes; dividing the melanocytes into at least two groups; treating a first group of melanocytes with at least one aromatic-cationic peptide; treating a second group of melanocytes with a vehicle control; assaying the first and second group of melanocytes for at least one therapeutic effect; and comparing the at least one therapeutic effect of the first group of melanocytes to the at least one therapeutic effect of the second group of melanocytes.

In some embodiments, the at least one therapeutic effect is one or more therapeutic effects selected from the group consisting of an increased mitochondrial membrane potential, an increased production of ATP, an increase in cell survival or proliferation, and an increase in melanin production.

In some embodiments, the assay also includes comparing the at least one therapeutic effect of the first group and second group of melanocytes to at least one therapeutic affect assayed from melanocytes from at least one subject not diagnosed with vitiligo.

In some embodiments, the subject is selected as a candidate for treatment based on one or more criteria selected from the group consisting of: the subject has a confirmed diagnosis of non-segmental vitiligo (NSV) with 15% to 50% of total body surface involvement, NSV involving the head and neck, stable or slowly progressive vitiligo over a 3-month period, the subject is at least 13 years old, and the subject has at least one vitiligo lesion measuring at least 2×2 cm in size.

In some embodiments, the subject is selected for treatment with at least one aromatic-cationic peptide if there is an increase of about 1% to 50%, 5% to 40%, 10% to 30%, or 15% to 25% in mitochondrial membrane potential, ATP production, in cell survival, cell proliferation, or melanin production in aromatic-cationic peptide treated melanocytes from the subject as compared to untreated melanocytes from the subject.

In some embodiments, the subject is selected for treatment with at least one aromatic-cationic peptide if the mitochondrial membrane potential, ATP production, cell survival, cell proliferation, or melanin production of aromatic-cationic peptide treated melanocytes from the subject return to normal levels by about 1% to 50%, 5% to 40%, 10% to 30%, or 15% to 25%, wherein normal levels of mitochondrial membrane potential, ATP production, cell survival, cell proliferation, or melanin production are established by assaying melanocytes from at least one subject not diagnosed with vitiligo.

In another aspect, the present technology provides for an assay for monitoring aromatic-cationic peptide treatment of a subject diagnosed with vitiligo, wherein the assay includes removing tissue from one or more affected skin areas of a vitiligo subject undergoing aromatic-cationic treatment, isolating the melanocytes from the tissues, culturing the isolated melanocytes, assaying the isolated melanocytes for at least one therapeutic effect, comparing the therapeutic effects to normalized levels of melanocytes cellular energetics, melanin production, and/or cell proliferation.

In some embodiments, the at least one therapeutic effect is one or more therapeutic effects selected from the group consisting of an increased mitochondrial membrane potential, an increased production of ATP, an increase in cell survival or proliferation, and an increase in melanin production.

In some embodiments, the assay also includes comparing the therapeutic effects of treatment with aromatic-cationic peptides to the original levels of melanocyte cellular energetics, melanin production, and/or cell proliferation from the vitiligo subject before treatment with the aromatic-cationic peptide.

In another aspect, the present technology provides for screening assay for determining the efficacy of a vitiligo therapy, the assay comprising removing tissue from an affected skin area of a subject diagnosed with vitiligo, isolating the melanocytes of from the tissue, culturing the isolated melanocytes, dividing the melanocytes into two or more groups, treating at least one of the groups of melanocytes with at least one aromatic-cationic peptide, treating at least one of the groups of melanocytes with a vehicle control, treating at least one group of melanocytes with the vitiligo therapy, assaying the melanocytes for a therapeutic effect by the treatment with aromatic-cationic peptide and the vitiligo therapy, and comparing the therapeutic effects of treatment with aromatic-cationic peptide to the therapeutic effects of treatment with the vitiligo therapy.

BRIEF DESCRIPTION OF DRAWINGS

FIG. 2 is a graph showing that treatment of melanocytes from human subjects diagnosed with vitiligo (VHM) with D-Arg-2',6'-Dmt-Lys-Phe-NH$_2$ at 2.0 μM for 3 days increased the ATP production of the treated VHM melanocytes as compared to untreated VHM melanocytes (i.e., 0 μM of D-Arg-2',6'-Dmt-Lys-Phe-NH$_2$).

DETAILED DESCRIPTION

Figure 1:
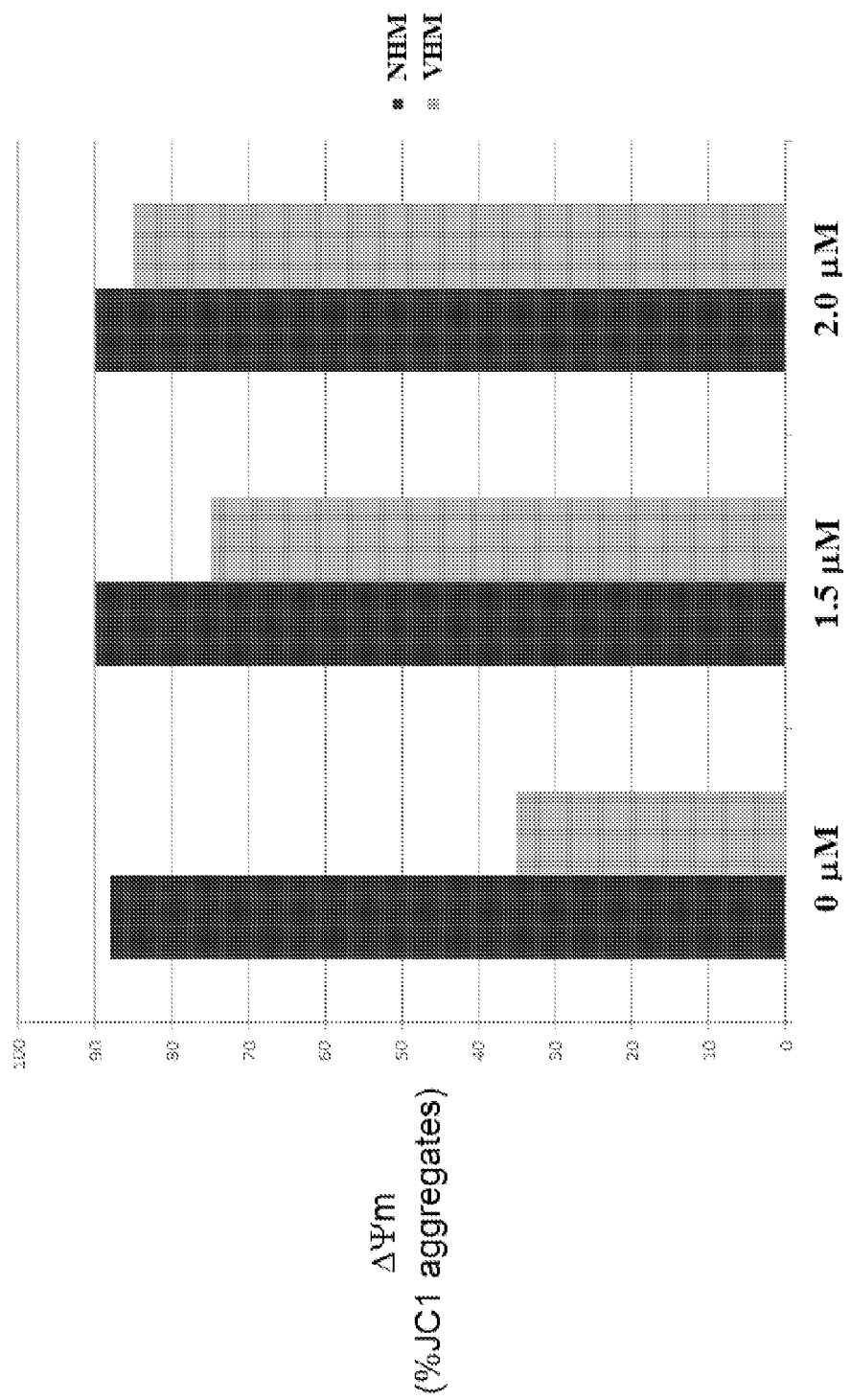
FIG. 1 is a graph showing that treatment of melanocytes from human subjects diagnosed with vitiligo (VHM) with D-Arg-2',6'-Dmt-Lys-Phe-NH$_2$ at 0 μM, 1.5 μM, and 2.0 μM for 7 days increased the mitochondrial membrane potential of the treated VHM. The mitochondrial membrane potential of treated and untreated VHM was compared to the mitochondrial potential of melanocytes from human subjects without vitiligo (NHM), which were also treated with D-Arg-2',6'-Dmt-Lys-Phe-NH$_2$ at 0 μM, 1.5 μM, and 2.0 μM for 7 days.

It is to be appreciated that certain aspects, modes, embodiments, variations and features of the present technology are described below in various levels of detail in order to provide a substantial understanding of the present technology. The present technology provides methods comprising administering aromatic-cationic peptides in effective amounts to treat or ameliorate the degeneration of melanocytes such as that found in a subject suffering from, or predisposed to vitiligo.

While the aromatic-cationic peptides described herein can occur and can be used as the neutral (non-salt) peptides, the description is intended to embrace all salts of the peptides described herein, as well as methods of using such salts of the peptides. In one embodiment, the salts of the peptides comprise pharmaceutically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). The desired salt of a basic peptide may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic peptides with amino acids, such as aspartate salts and glutamate salts, can also be prepared. The desired salt of an acidic peptide can be prepared by methods known to those of skill in the art by treating the compound with a base. Examples of inorganic salts of acidic peptides include, but are not limited to, alkali metal and alkaline earth salts, such as sodium salts, potassium salts, magnesium salts, and calcium salts; ammonium salts; and aluminum salts.

Examples of organic salts of acid peptides include, but are not limited to, procaine, dibenzylamine, N-ethylpiperidine, N,N'-dibenzylethylenediamine, and triethylamine salts. Salts of acidic peptides with amino acids, such as lysine salts, can also be prepared. The present technology also includes all stereoisomers and geometric isomers of the peptides, including diastereomers, enantiomers, and cis/trans (E/Z) isomers. The present technology also includes mixtures of stereoisomers and/or geometric isomers in any ratio, including, but not limited to, racemic mixtures.

Definitions

The definitions of certain terms as used in this specification are provided below. Unless defined otherwise, all technical and scientific terms used herein generally have the same meaning as commonly understood by one of ordinary skill in the art to which this present technology belongs.

As used in this specification and the appended claims, the singular forms "a", "an" and "the" include plural referents unless the content clearly dictates otherwise. For example, reference to "a cell" includes a combination of two or more cells, and the like.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. In some embodiments, the aromatic-cationic peptide is administered by an intracoronary route or an intra-arterial route. Administration includes self-administration and the administration by another.

As used herein, the term "amino acid" is used to refer to any organic molecule that contains at least one amino group and at least one carboxyl group. Typically, at least one amino group is at the α position relative to a carboxyl group. The term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refer to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the term "effective amount" refers to a quantity sufficient to achieve a desired therapeutic and/or prophylactic effect, e.g., an amount which results in the prevention of, or a decrease in, one or more symptoms associated with melanocyte degeneration. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan would be able to determine appropriate dosages depending on these and other factors. The compositions can also be administered in combination with one or more additional therapeutic compounds. In the methods described herein, the aromatic-cationic peptides may be administered to a subject having one or more signs or symptoms of melanocyte degeneration. For example, a "therapeutically effective amount" of the aromatic-cationic peptides means levels in which the physiological effects of melanocyte degeneration are, at a minimum, ameliorated. A therapeutically effective amount can be given in one or more administrations. In some embodiments, signs, symptoms or complications of vitiligo include, but are not limited to, increased photosensitivity, decreased contact sensitivity response to dinitrochlorobenzene, depigmentation of the skin, mucous membranes, retina, or genitals, and premature whitening or graying of hair on the scalp, eyelashes, eyebrows or beard.

An "isolated" or "purified" polypeptide or peptide is substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with diagnostic or therapeutic uses of the agent. Such interfering materials may include enzymes, hormones and other proteinaceous and nonproteinaceous solutes.

As used herein, the term "net charge" refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

As used herein, the terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, "prevention" or "preventing" of a disorder or condition refers to a compound that, in a statistical sample, reduces the occurrence of the disorder or condition in the sample relative to a control sample, or delays the onset or reduces the severity of one or more symptoms of the disorder or condition relative to the control sample. As used herein, preventing vitiligo includes preventing an autoimmune response, suppressing cytotoxicity and apoptosis associated with exposure to 4-tertiary butyl phenol, or inhibiting progressive depigmentation of hair or epidermal cells, thereby preventing or ameliorating the harmful effects of melanocyte degeneration.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

As used herein, the terms "subject," "individual," or "patient" can be an individual organism, a vertebrate, a mammal, or a human.

A "synergistic therapeutic effect" refers to a greater-than-additive therapeutic effect which is produced by a combination of two agents, and which exceeds that which would otherwise result from individual administration of either agent alone. Therefore, lower doses of one or both of the agents may be used in treating vitiligo, resulting in increased therapeutic efficacy and decreased side-effects.

As used herein, the terms "treating" or "treatment" or "alleviation" refers to therapeutic treatment, wherein the object is to slow down (lessen) the targeted pathologic condition or disorder. A subject is successfully "treated" for vitiligo if, after receiving a therapeutic amount of the aromatic-cationic peptides according to the methods described herein, the subject shows observable and/or measurable reduction in melanocyte degeneration. It is also to be appreciated that the various modes of treatment of medical conditions as described are intended to mean "substantial", which includes total but also less than total treatment, and wherein some biologically or medically relevant result is achieved.

Pathogenesis of Vitiligo

Vitiligo is a pigmentation disorder in which melanocytes, the cells responsible for skin pigmentation, are destroyed. As a result, white patches appear on the skin in different parts of the body. Although patches are initially small, they often enlarge and change shape. Vitiligo lesions can appear anywhere, but are most commonly found on the acral areas, mucous membranes (tissues that line the inside of the mouth and nose), retina and genitals. Other symptoms include increased photosensitivity, decreased contact sensitivity response to dinitrochlorobenzene, and premature whitening or graying of hair that grows on areas affected by vitiligo. A Black light can be used in the early phase of this disease for identification and to determine effectiveness of treatment. Skin with vitiligo, when exposed to a Black light, will glow yellow, green or blue, in contrast to healthy skin which will have no reaction.

Non-segmental vitiligo (NSV) is associated with some form of symmetry in the location of the patches of depigmentation. Classes of NSV include generalized vitiligo, universal vitiligo, acrofacial vitiligo, mucosal vitiligo, and focal vitiligo. Generalized vitiligo (GV), the most common category, affects approximately 0.5% of the world's population, with an average age of onset at about 24 years and occurring with approximately equal frequencies in males and females. While there is no variation by ethnicity, the disease can be much more apparent and thus emotionally distressing for individuals with darker skin colors.

Segmental vitiligo (SV) differs in appearance, cause and prevalence than NVS. SV tends to affect areas of skin that are associated with dorsal roots from the spinal cord and is most often unilateral. SV spreads much more rapidly than NSV and, without treatment, SV is much more stable/static in course and is not associated with auto-immune diseases.

Vitiligo lesions have an infiltrate of inflammatory cells, particularly cytotoxic and helper T cells and macrophages. Patients with vitiligo are also more likely to have at least one other autoimmune disease including Hashimoto's thyroiditis, Graves' disease, pernicious anemia, rheumatoid arthritis, psoriasis, type I diabetes, Addison's disease, celiac disease, inflammatory bowel disorder, and systemic lupus erythematosus. Furthermore, recent genome-wide association studies of GV have identified a total of 17 confirmed GV susceptibility loci: NLRP1, TYR, HLA class I, HLA class II, HLA class III, PTPN22, XBP1, IL2RA, LPP, RERE, FOXP1, TSLP, CCR6, GZMB, UBASH3A, C1QTNF6, and FOXP3. Virtually all of these susceptibility loci encode known immunoregulatory proteins, and many have been associated with genetic susceptibility to other autoimmune diseases that are epidemiologically linked to GV. The one exception is TYR, which encodes tyrosinase, the key enzyme of melanin biosynthesis in melanocytes and the major autoantigen in GV. Nevertheless, the specific triggers of the autoimmune response in GV have yet to be identified because autoantigens by themselves normally do not generate harmful immune responses.

The exact etiology of vitiligo is unknown. However, epidemiological evidence indicates that vitiligo is a complex disease involving both genetic predisposition and unknown environmental triggers. About 30 percent of people with vitiligo have a family member with the disease. However, only 5 to 7 percent of children will get vitiligo even if a parent has it, and most people with vitiligo do not have a family history of the disorder. Thus, GV takes on a non-Mendelian pattern that is suggestive of polygenic, multifactorial inheritance. These data indicate that genetic factors are of considerable importance in determining one's susceptibility to vitiligo. Nevertheless, twin studies have shown that although genes play an important role in disease pathogenesis, non-genetic factors are just as, if not more, important. Although many different environmental risk factors for GV have been proposed, the exact mechanisms whereby melanocytes disappear or become nonfunctional remain obscure.

The present technology relates to treating or ameliorating melanocyte degeneration in a subject in need thereof, by administering aromatic-cationic peptides as disclosed herein such as D-Arg-2',6'-Dmt-Lys-Phe-NH$_2$, or pharmaceutically acceptable salts thereof, such as acetate salt, tartrate salt, or trifluoroacetate salt. The present technology relates to the treatment, amelioration or prevention of vitiligo in mammals through administration of therapeutically effective amounts of aromatic-cationic peptides as disclosed herein, such as D-Arg-2',6'-Dmt-Lys-Phe-NH$_2$, or pharmaceutically acceptable salts thereof, such as acetate salt, tartrate salt, or trifluoroacetate salt, to subjects in need thereof.

Aromatic-Cationic Peptides of the Present Technology

The aromatic-cationic peptides of the present technology are water-soluble and highly polar. Despite these properties, the peptides can readily penetrate cell membranes. The aromatic-cationic peptides typically include a minimum of three amino acids or a minimum of four amino acids, covalently joined by peptide bonds. The maximum number of amino acids present in the aromatic-cationic peptides is about twenty amino acids covalently joined by peptide bonds. Suitably, the maximum number of amino acids is about twelve, or about nine, or about six.

In some aspects, the present technology provides an aromatic-cationic peptide or a pharmaceutically acceptable salt thereof such as acetate salt, tartrate salt, or trifluoroacetate salt. In some embodiments, the peptide comprises at least one net positive charge; a minimum of three amino acids; a maximum of about twenty amino acids;

a relationship between the minimum number of net positive charges ($p_m$) and the total number of amino acid residues (r) wherein $3p_m$ is the largest number that is less than or equal to r+1; and a relationship between the minimum number of aromatic groups (a) and the total number of net positive charges ($p_t$) wherein 2a is the largest number that is less than or equal to $p_t+1$, except that when a is 1, $p_t$ may also be 1.

In some embodiments, the peptide comprises the amino acid sequence Phe-D-Arg-Phe-Lys-NH$_2$ or D-Arg-2'6'-Dmt-Lys-Phe-NH$_2$. In some embodiments, the peptide comprises one or more of the peptides of Table 5 (see below):

In one embodiment, the aromatic-cationic peptide is defined by formula I.

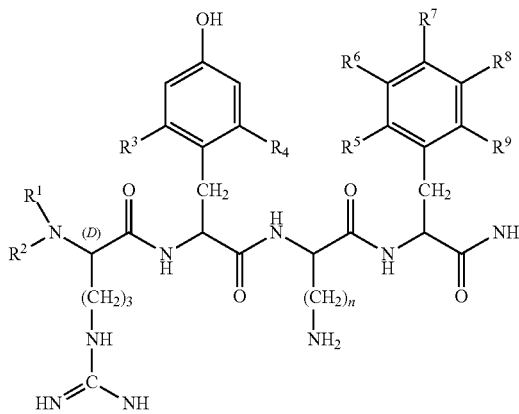

wherein $R^1$ and $R^2$ are each independently selected from
(i) hydrogen;
(ii) linear or branched $C_1$-$C_6$ alkyl;

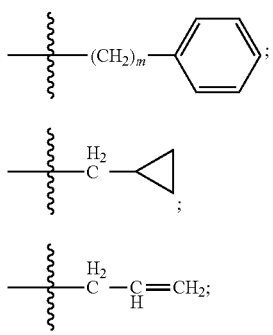

where m = 1-3

$R^3$ and $R^4$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo;
$R^5$, $R^6$, $R^7$, $R^8$, and $R^9$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and
n is an integer from 1 to 5.

In a particular embodiment, $R^1$ and $R^2$ are hydrogen; $R^3$ and $R^4$ are methyl; $R^5$, $R^6$, $R^7$, $R^8$, and $R^9$ are all hydrogen; and n is 4.

In one embodiment, the peptide is defined by formula II:

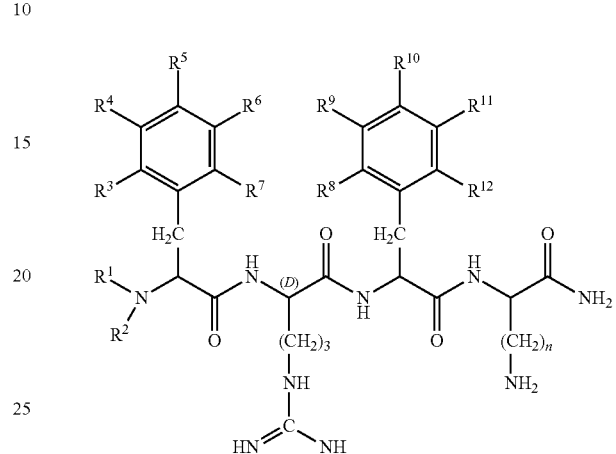

wherein $R^1$ and $R^2$ are each independently selected from
(i) hydrogen;
(ii) linear or branched $C_1$-$C_6$ alkyl;

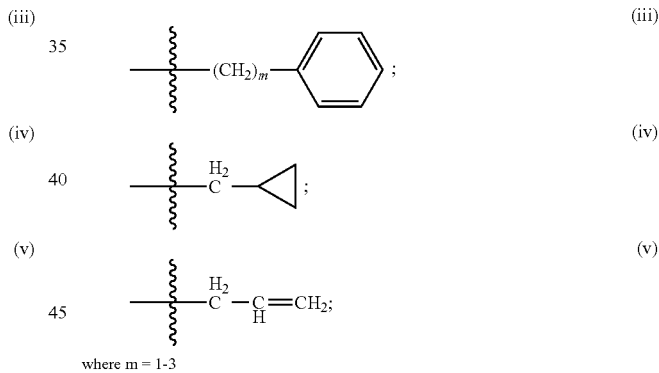

where m = 1-3

$R^3$, $R^4$, $R^5$, $R^6$, $R^7$, $R^8$, $R^9$, $R^{10}$, $R^{11}$ and $R^{12}$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and
n is an integer from 1 to 5.

In a particular embodiment, $R^1$, $R^2$, $R^3$, $R^4$, $R^5$, $R^6$, $R^7$, $R^8$, $R^9$, $R^{10}$, $R^{11}$, and $R^{12}$ are all hydrogen; and n is 4. In another embodiment, $R^1$, $R^2$, $R^3$, $R^4$, $R^5$, $R^6$, $R^7$, $R^9$, and $R^{11}$ are all hydrogen; $R^8$ and $R^{12}$ are methyl; $R^{10}$ is hydroxyl; and n is 4.

In one embodiment, the aromatic-cationic peptides of the present technology have a core structural motif of alternating aromatic and cationic amino acids. For example, the peptide may be a tetrapeptide defined by any of formulas III to VI set forth below:

| | |
|---|---|
| Aromatic-Cationic-Aromatic-Cationic | (Formula III) |
| Cationic-Aromatic-Cationic-Aromatic | (Formula IV) |
| Aromatic-Aromatic-Cationic-Cationic | (Formula V) |
| Cationic-Cationic-Aromatic-Aromatic | (Formula VI) | wherein, aromatic is a residue selected from the group consisting of: Phe (F), Tyr (Y), Trp (W), and Cyclohexyl-alanine (Cha); and Cationic is a residue selected from the group consisting of: Arg (R), Lys (K), Norleucine (Nle), and 2-amino-heptanoic acid (Ahe).

The peptides disclosed herein may be formulated as pharmaceutically acceptable salts. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the salt is an acetate salt. Additionally or alternatively, in some embodiments, the salt is a trifluoroacetate salt. Additionally or alternatively, in some embodiments, the salt is a tartrate salt.

The aromatic-cationic peptides of the present technology disclosed herein may be synthesized by any of the methods well known in the art. Suitable methods for chemically synthesizing the protein include, for example, liquid phase and solid phase synthesis, and those methods described by Stuart and Young in *Solid Phase Peptide Synthesis*, Second Edition, Pierce Chemical Company (1984), and in *Methods Enzymol.*, 289, Academic Press, Inc., New York (1997). Recombinant peptides may be generated using conventional techniques in molecular biology, protein biochemistry, cell biology, and microbiology, such as those described in *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, Meth. Enzymol. (Academic Press, Inc., 1984); *Gene Transfer Vectors for Mammalian Cells*, Miller & Calos, Eds. (Cold Spring Harbor Laboratory, N Y, 1987); and *Meth. Enzymol.*, Vols. 154 and 155, Wu & Grossman, and Wu, Eds., respectively.

Aromatic-cationic peptide precursors may be made by either chemical (e.g., using solution and solid phase chemical peptide synthesis) or recombinant syntheses known in the art. Precursors of e.g., amidated aromatic-cationic peptides of the present technology may be made in like manner. In some embodiments, recombinant production is believed significantly more cost effective. In some embodiments, precursors are converted to active peptides by amidation reactions that are also known in the art. For example, enzymatic amidation is described in U.S. Pat. No. 4,708,934 and European Patent Publications 0 308 067 and 0 382 403. Recombinant production can be used for both the precursor and the enzyme that catalyzes the conversion of the precursor to the desired active form of the aromatic-cationic peptide. Such recombinant production is discussed in Biotechnology, Vol. 11 (1993) pp. 64-70, which further describes a conversion of a precursor to an amidated product. During amidation, a keto-acid such as an alpha-keto acid, or salt or ester thereof, wherein the alpha-keto acid has the molecular structure RC(O)C(O)OH, and wherein R is selected from the group consisting of aryl, a C1-C4 hydrocarbon moiety, a halogenated or hydroxylated C1-C4 hydrocarbon moiety, and a C1-C4 carboxylic acid, may be used in place of a catalase co-factor. Examples of these keto acids include, but are not limited to, ethyl pyruvate, pyruvic acid and salts thereof, methyl pyruvate, benzoyl formic acid and salts thereof, 2-ketobutyric acid and salts thereof, 3-methyl-2-oxobutanoic acid and salts thereof, and 2-keto glutaric acid and salts thereof.

In some embodiments, the production of the recombinant aromatic-cationic peptide may proceed, for example, by producing glycine-extended precursor in *E. coli* as a soluble fusion protein with glutathione-S-transferase. An α-amidating enzyme catalyzes conversion of precursors to active aromatic-cationic peptide. That enzyme is recombinantly produced, for example, in Chinese Hamster Ovary (CHO) cells as described in the Biotechnology article cited above. Other precursors to other amidated peptides may be produced in like manner. Peptides that do not require amidation or other additional functionalities may also be produced in like manner. Other peptide active agents are commercially available or may be produced by techniques known in the art.

The peptides optionally contain one or more non-naturally occurring amino acids. Optimally, the peptide has no amino acids that are naturally occurring. The non-naturally occurring amino acids may be levorotary (L-), dextrorotary (D-), or mixtures thereof. Non-naturally occurring amino acids are those amino acids that typically are not synthesized in normal metabolic processes in living organisms, and do not naturally occur in proteins. In addition, the non-naturally occurring amino acids suitably are also not recognized by common proteases. The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups not found in natural amino acids. Some examples of non-natural alkyl amino acids include α-aminobutyric acid, β-aminobutyric acid, γ-aminobutyric acid, δ-aminovaleric acid, and ε-aminocaproic acid. Some examples of non-natural aryl amino acids include ortho-, meta, and para-aminobenzoic acid. Some examples of non-natural alkylaryl amino acids include ortho-, meta-, and para-aminophenylacetic acid, and γ-phenyl-β-aminobutyric acid. Non-naturally occurring amino acids include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched C1-C4 alkyl, such as methyl, ethyl, n-propyl, isopropyl, butyl, isobutyl, or t-butyl, C1-C4 alkyloxy (i.e., alkoxy), amino, C1-C4 alkylamino and C1-C4 dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva) and norleucine (Nle).

Another example of a modification of an amino acid in a peptide is the derivatization of a carboxyl group of an aspartic acid or a glutamic acid residue of the peptide. One example of derivatization is amidation with ammonia or with a primary or secondary amine, e.g. methylamine, ethylamine, dimethylamine or diethylamine. Another example of derivatization includes esterification with, for example, methyl or ethyl alcohol. Another such modification includes derivatization of an amino group of a lysine, arginine, or histidine residue. For example, such amino groups can be acylated. Some suitable acyl groups include, for example, a benzoyl group or an alkanoyl group comprising any of the C1-C4 alkyl groups mentioned above, such as an acetyl or propionyl group.

The non-naturally occurring amino acids are suitably resistant or insensitive to common proteases. Examples of non-naturally occurring amino acids that are resistant or insensitive to proteases include the dextrorotatory (D-) form of any of the above-mentioned naturally occurring L-amino acids, as well as L- and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides should have less than five, or less than four, or less than three, or less than two contiguous L-amino acids recognized by common proteases, irrespective of whether the amino acids are naturally or non-naturally occurring. Optimally, the peptide has only D-amino acids, and no L-amino acids. If the peptide contains protease sensitive sequences of amino acids, at least one of the amino acids is a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

The aromatic-cationic peptides should have a minimum number of net positive charges at physiological pH in comparison to the total number of amino acid residues in the peptide. The minimum number of net positive charges at physiological pH will be referred to below as (pm). The total number of amino acid residues in the peptide will be referred to below as (r). The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

Typically, a peptide has a positively charged N-terminal amino group and a negatively charged C-terminal carboxyl group. The charges cancel each other out at physiological pH. As an example of calculating net charge, the peptide Tyr-Arg-Phe-Lys-Glu-His-Trp-D-Arg has one negatively charged amino acid (i.e., Glu) and four positively charged amino acids (i.e., two Arg residues, one Lys, and one His). Therefore, the above peptide has a net positive charge of three.

In one embodiment, the aromatic-cationic peptides have a relationship between the minimum number of net positive charges at physiological pH (pm) and the total number of amino acid residues (r) wherein 3pm is the largest number that is less than or equal to r+1. In this embodiment, the relationship between the minimum number of net positive charges (pm) and the total number of amino acid residues (r) is as follows:

TABLE 1

Amino acid number and net positive charges ($3p_m \leq p + 1$)

| | | | | | | | | (r) | | | | | | | | | | |
|---|---|---|---|---|---|---|---|---|---|---|---|---|---|---|---|---|---|---|
| | 3 | 4 | 5 | 6 | 7 | 8 | 9 | 10 | 11 | 12 | 13 | 14 | 15 | 16 | 17 | 18 | 19 | 20 |
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges (pm) and the total number of amino acid residues (r) wherein 2pm is the largest number that is less than or equal to r+1. In this embodiment, the relationship between the minimum number of net positive charges (pm) and the total number of amino acid residues (r) is as follows:

TABLE 2

Amino acid number and net positive charges ($2p_m \leq p + 1$)

| | | | | | | | | (r) | | | | | | | | | | |
|---|---|---|---|---|---|---|---|---|---|---|---|---|---|---|---|---|---|---|
| | 3 | 4 | 5 | 6 | 7 | 8 | 9 | 10 | 11 | 12 | 13 | 14 | 15 | 16 | 17 | 18 | 19 | 20 |
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges (pm) and the total number of amino acid residues (r) are equal. In another embodiment, the peptides have three or four amino acid residues and a minimum of one net positive charge, or a minimum of two net positive charges, or a minimum of three net positive charges.

It is also important that the aromatic-cationic peptides have a minimum number of aromatic groups in comparison to the total number of net positive charges (pt). The minimum number of aromatic groups will be referred to below as (a). Naturally occurring amino acids that have an aromatic group include the amino acids histidine, tryptophan, tyrosine, and phenylalanine. For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

The aromatic-cationic peptides should also have a relationship between the minimum number of aromatic groups (a) and the total number of net positive charges at physiological pH (pt) wherein 3a is the largest number that is less than or equal to pt+1, except that when pt is 1, a may also be 1. In this embodiment, the relationship between the minimum number of aromatic groups (a) and the total number of net positive charges (pt) is as follows:

TABLE 3

Aromatic groups and net positive charges ($3a \leq p_t + 1$ or $a = p_t = 1$)

| | | | | | | | | | ($p_t$) | | | | | | | | | | |
|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges (n) wherein 2a is the largest number that is less than or equal to $p_t$+1. In this embodiment, the relationship between the minimum number of aromatic amino acid residues (a) and the total number of net positive charges ($p_t$) is as follows:

TABLE 4

Aromatic groups and net positive charges ($2a \leq p_t + 1$ or $a = p_t = 1$)

| | ($p_t$) | | | | | | | | | | | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal.

Carboxyl groups, especially the terminal carboxyl group of a C-terminal amino acid, are suitably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group. The free carboxylate groups of the asparagine, glutamine, aspartic acid, and glutamic acid residues not occurring at the C-terminus of the aromatic-cationic peptides may also be amidated wherever they occur within the peptide. The amidation at these internal positions may be with ammonia or any of the primary or secondary amines described above.

In one embodiment, the aromatic-cationic peptide is a tripeptide having two net positive charges and at least one aromatic amino acid. In a particular embodiment, the aromatic-cationic peptide is a tripeptide having two net positive charges and two aromatic amino acids.

Aromatic-cationic peptides include, but are not limited to, the following peptide examples:

TABLE 5

Exemplary Aromatic-Cationic Peptides

D-Arg-2',6'-Dmt-Lys-Phe-NH$_2$
Phe-D-Arg-Phe-Lys-NH$_2$
Phe-Lys-Dmt-D-Arg-NH$_2$
2',6'-Dmp-D-Arg-Phe-Lys-NH$_2$
D-Arg-Dmt-Phe-Lys-NH$_2$
D-Arg-Phe-Lys-Dmt-NH$_2$
D-Arg-Phe-Dmt-Lys-NH$_2$
D-Arg-Lys-Dmt-Phe-NH$_2$
D-Arg-Lys-Phe-Dmt-NH$_2$
Phe-Lys-D-Arg-Dmt-NH$_2$
Phe-D-Arg-Lys-Dmt-NH$_2$
Phe-Dmt-D-Arg-Lys-NH$_2$
Phe-Dmt-Lys-D-Arg-NH$_2$
Lys-Phe-Dmt-D-Arg-NH$_2$
Lys-Dmt-D-Arg-Phe-NH$_2$
Lys-Dmt-Phe-D-Arg-NH$_2$
Lys-D-Arg-Phe-Dmt-NH$_2$
Lys-D-Arg-Dmt-Phe-NH$_2$
D-Arg-Dmt-D-Arg-Phe-NH$_2$
D-Arg-Dmt-D-Arg-Dmt-NH$_2$
D-Arg-Dmt-D-Arg-Tyr-NH$_2$
D-Arg-Dmt-D-Arg-Trp-NH$_2$
Trp-D-Arg-Phe-Lys-NH$_2$
Trp-D-Arg-Tyr-Lys-NH$_2$
Trp-D-Arg-Trp-Lys-NH$_2$
Trp-D-Arg-Dmt-Lys-NH$_2$
D-Arg-Trp-Lys-Phe-NH$_2$
D-Arg-Trp-Phe-Lys-NH$_2$
D-Arg-Trp-Lys-Dmt-NH$_2$
D-Arg-Trp-Dmt-Lys-NH$_2$
D-Arg-Lys-Trp-Phe-NH$_2$
D-Arg-Lys-Trp-Dmt-NH$_2$
Cha-D-Arg-Phe-Lys-NH$_2$
Ala-D-Arg-Phe-Lys-NH$_2$
2',6'-Dmt-D-Arg-Phe-Lys-NH$_2$
Phe-D-Arg-Dmt-Lys-NH$_2$
Lys-D-Arg-Tyr-NH$_2$
Phe-D-Arg-His
D-Tyr-Trp-Lys-NH$_2$
Trp-D-Lys-Tyr-Arg-NH$_2$
Tyr-His-D-Gly-Met
Phe-Arg-D-His-Asp
Tyr-D-Arg-Phe-Lys-Glu-NH$_2$
Met-Tyr-D-Lys-Phe-Arg
D-His-Glu-Lys-Tyr-D-Phe-Arg
Lys-D-Gln-Tyr-Arg-D-Phe-Trp-NH$_2$
Phe-D-Arg-Lys-Trp-Tyr-D-Arg-His
Gly-D-Phe-Lys-Tyr-His-D-Arg-Tyr-NH$_2$
Val-D-Lys-His-Tyr-D-Phe-Ser-Tyr-Arg-NH$_2$
Trp-Lys-Phe-D-Asp-Arg-Tyr-D-His-Lys
Lys-Trp-D-Tyr-Arg-Asn-Phe-Tyr-D-His-NH$_2$
Thr-Gly-Tyr-Arg-D-His-Phe-Trp-D-His-Lys
Asp-D-Trp-Lys-Tyr-D-His-Phe-Arg-D-Gly-Lys-NH$_2$
D-His-Lys-Tyr-D-Phe-Glu-D-Asp-D-His-D-Lys-Arg-Trp-NH$_2$
Ala-D-Phe-D-Arg-Tyr-Lys-D-Trp-His-D-Tyr-Gly-Phe
Tyr-D-His-Phe-D-Arg-Asp-Lys-D-Arg-His-Trp-D-His-Phe
Phe-Phe-D-Tyr-Arg-Glu-Asp-D-Lys-Arg-D-Arg-His-Phe-NH$_2$
Phe-Try-Lys-D-Arg-Trp-His-D-Lys-D-Lys-Glu-Arg-D-Tyr-Thr
Tyr-Asp-D-Lys-Tyr-Phe-D-Lys-D-Arg-Phe-Pro-D-Tyr-His-Lys
Glu-Arg-D-Lys-Tyr-D-Val-Phe-D-His-Trp-Arg-D-Gly-Tyr-Arg-D-Met-NH$_2$
Arg-D-Leu-D-Tyr-Phe-Lys-Glu-D-Lys-Arg-D-Trp-Lys-D-Phe-Tyr-D-Arg-Gly
D-Glu-Asp-Lys-D-Arg-D-His-Phe-Phe-D-Val-Tyr-Arg-Tyr-D-Tyr-Arg-His-Phe-NH$_2$
Asp-Arg-D-Phe-Cys-Phe-D-Arg-D-Lys-Tyr-Arg-D-Tyr-Trp-D-His-Tyr-D-Phe-Lys-Phe
His-Tyr-D-Arg-Trp-Lys-Phe-D-Asp-Ala-Arg-Cys-D-Tyr-His-Phe-D-Lys-Tyr-His-Ser-NH$_2$
Gly-Ala-Lys-Phe-D-Lys-Glu-Arg-Tyr-His-D-Arg-D-Arg-Asp-Tyr-Trp-D-His-Trp-His-D-Lys-Asp
Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH$_2$
Tyr-D-Arg-Phe-Lys-NH$_2$
Tyr-Arg-Phe-Lys-Glu-His-Trp-Arg (SEQ ID NO: 1)
Lys-Gln-Tyr-Arg-Phe-Trp (SEQ ID NO: 2)
Dmt-D-Arg-Phe-A$_2$bu-NH$_2$
Dmt-D-Arg-Phe(p-F)-Lys-NH$_2$
Dmt(NMe)-D-Arg-Phe-Lys-NH$_2$
H-Tyr-D-Ala-Gly-MePhe(d5)-Gly-ol
H-Tyr-D-Arg-Phe(d$_5$)-Lys-NH$_2$
H-Dmt-D-Arg-Phe(d$_5$)Lys-NH$_2$
2',6'-Dmt-D-Arg-Ald-Lys-NH$_2$
2',6'-Dmt-D-Arg-Phe-Lys-Ald-NH$_2$
D-Arg-Tyr-Lys-Phe-NH$_2$
Tyr-D-Arg-Phe-Orn-NH$_2$
Tyr-D-Arg-Phe-Dab-NH$_2$
Tyr-D-Arg-Phe-Dap-NH$_2$
2',6'-Dmt-D-Arg-Phe-Lys-NH(CH$_2$)$_2$—NH-dns-NH$_2$
2',6'-Dmt-D-Arg-Phe-Lys-NH(CH$_2$)$_2$—NH-atn-NH$_2$
2',6'-Dmt-D-Arg-Phe-dnsLys-NH$_2$
2',6'-Dmt-D-Cit-Phe-Lys-NH$_2$
2',6'-Dmt-D-Cit-Phe-Ahp-NH$_2$
2',6'-Dmt-D-Arg-Phe-Orn-NH$_2$ TABLE 5-continued Exemplary Aromatic-Cationic Peptides 2',6'-Dmt-D-Arg-Phe-Dab-NH$_2$
2'6-'Dmt-D-Arg-Phe-Dap-NH$_2$
2',6'-Dmt-D-Arg-Phe-Ahp(2-aminoheptanoic acid)-NH$_2$
Bio-2',6'-Dmt-D-Arg-Phe-Lys-NH$_2$
3',5'-Dmt-D-Arg-Phe-Lys-NH$_2$
3',5'-Dmt-D-Arg-Phe-Orn-NH$_2$
3',5'-Dmt-D-Arg-Phe-Dab-NH$_2$
3',5'-Dmt-D-Arg-Phe-Dap-NH$_2$
Tyr-D-Arg-Tyr-Lys-NH$_2$
Tyr-D-Arg-Tyr-Orn-NH$_2$
Tyr-D-Arg-Tyr-Dab-NH$_2$
Tyr-D-Arg-Tyr-Dap-NH$_2$
2',6'-Dmt-D-Arg-Tyr-Lys-NH$_2$
2',6'-Dmt-D-Arg-Tyr-Orn-NH$_2$
2',6'-Dmt-D-Arg-Tyr-Dab-NH$_2$
2',6'-Dmt-D-Arg-Tyr-Dap-NH$_2$
2',6'-Dmt-D-Arg-2',6'-Dmt-Lys-NH$_2$
2',6'-Dmt-D-Arg-2',6'-Dmt-Orn-NH$_2$
2',6'-Dmt-D-Arg-2',6'-Dmt-Dab-NH$_2$
2',6'-Dmt-D-Arg-2',6'-Dmt-Dap-NH$_2$
3',5'-Dmt-D-Arg-3',5'-Dmt-Arg-NH$_2$
3',5'-Dmt-D-Arg-3',5'-Dmt-Lys-NH$_2$
3',5'-Dmt-D-Arg-3',5'-Dmt-Orn-NH$_2$
3',5'-Dmt-D-Arg-3',5'-Dmt-Dab-NH$_2$
Tyr-D-Lys-Phe-Dap-NH$_2$
Tyr-D-Lys-Phe-Arg-NH$_2$
Tyr-D-Lys-Phe-Lys-NH$_2$
Tyr-D-Lys-Phe-Orn-NH$_2$
2',6'-Dmt-D-Lys-Phe-Dab-NH$_2$
2',6'-Dmt-D-Lys-Phe-Dap-NH$_2$
2',6'-Dmt-D-Lys-Phe-Arg-NH$_2$
2',6'-Dmt-D-Lys-Phe-Lys-NH$_2$
3',5'-Dmt-D-Lys-Phe-Orn-NH$_2$
3',5'-Dmt-D-Lys-Phe-Dab-NH$_2$
3',5'-Dmt-D-Lys-Phe-Dap-NH$_2$
3',5'-Dmt-D-Lys-Phe-Arg-NH$_2$
Tyr-D-Lys-Tyr-Lys-NH$_2$
Tyr-D-Lys-Tyr-Orn-NH$_2$
Tyr-D-Lys-Tyr-Dab-NH$_2$
Tyr-D-Lys-Tyr-Dap-NH$_2$
2',6'-Dmt-D-Lys-Tyr-Lys-NH$_2$
2',6'-Dmt-D-Lys-Tyr-Orn-NH$_2$
2',6'-Dmt-D-Lys-Tyr-Dab-NH$_2$
2',6'-Dmt-D-Lys-Tyr-Dap-NH$_2$
2',6'-Dmt-D-Lys-2',6'-Dmt-Lys-NH$_2$
2',6'-Dmt-D-Lys-2',6'-Dmt-Orn-NH$_2$
2',6'-Dmt-D-Lys-2',6'-Dmt-Dab-NH$_2$
2',6'-Dmt-D-Lys-2',6'-Dmt-Dap-NH$_2$
2',6'-Dmt-D-Arg-Phe-dnsDap-NH$_2$
2',6'-Dmt-D-Arg-Phe-atnDap-NH$_2$
3',5'-Dmt-D-Lys-3',5'-Dmt-Lys-NH$_2$
3',5'-Dmt-D-Lys-3',5'-Dmt-Orn-NH$_2$
3',5'-Dmt-D-Lys-3',5'-Dmt-Dab-NH$_2$
3',5'-Dmt-D-Lys-3',5'-Dmt-Dap-NH$_2$
Tyr-D-Orn-Phe-Arg-NH$_2$
Tyr-D-Dab-Phe-Arg-NH$_2$
Tyr-D-Dap-Phe-Arg-NH$_2$
2',6'-Dmt-D-Arg-Phe-Arg-NH$_2$
2',6'-Dmt-D-Orn-Phe-Arg-NH$_2$
2',6'-Dmt-D-Dab-Phe-Arg-NH$_2$
3',5'-Dmt-D-Dap-Phe-Arg-NH$_2$
3',5'-Dmt-D-Arg-Phe-Arg-NH$_2$
3',5'-Dmt-D-Orn-Phe-Arg-NH$_2$
Tyr-D-Lys-Tyr-Arg-NH$_2$
Tyr-D-Orn-Tyr-Arg-NH$_2$
Tyr-D-Dab-TyrArg-NH$_2$
Tyr-D-Dap-Tyr-Arg-NH$_2$
2',6'-Dmt-D-Arg-2',6'-Dmt-Arg-NH$_2$
2',6'-Dmt-D-Lys-2',6'-Dmt-Arg-NH$_2$
2',6'-Dmt-D-Orn-2',6'-Dmt-Arg-NH$_2$
2',6'-Dmt-D-Dab-2',6'-Dmt-Arg-NH$_2$
3',5'-Dmt-D-Dap-3',5'-Dmt-Arg-NH$_2$
3',5'-Dmt-D-Lys-3',5'-Dmt-Arg-NH$_2$
3',5'-Dmt-D-Orn-3',5'-Dmt-Arg-NH$_2$
Mmt-D-Arg-Phe-Lys-NH$_2$
Mmt-D-Arg-Phe-Orn-NH$_2$
Mmt-D-Arg-Phe-Dab-NH$_2$
Mmt-D-Arg-Phe-Dap-NH$_2$
Tmt-D-Arg-Phe-Lys-NH$_2$
Tmt-D-Arg-Phe-Orn-NH$_2$
Tmt-D-Arg-Phe-Dab-NH$_2$
Tmt-D-Arg-Phe-Dap-NH$_2$
Hmt-D-Arg-Phe-Lys-NH$_2$
Hmt-D-Arg-Phe-Orn-NH$_2$
Hmt-D-Arg-Phe-Dab-NH$_2$
Hmt-D-Arg-Phe-Dap-NH$_2$
Mmt-D-Lys-Phe-Lys-NH$_2$
Mmt-D-Lys-Phe-Orn-NH$_2$
Mmt-D-Lys-Phe-Dab-NH$_2$
Mmt-D-Lys-Phe-Dap-NH$_2$
Mmt-D-Lys-Phe-Arg-NH$_2$
Tmt-D-Lys-Phe-Lys-NH$_2$
Tmt-D-Lys-Phe-Orn-NH$_2$
Tmt-D-Lys-Phe-Dab-NH$_2$
Tmt-D-Lys-Phe-Dap-NH$_2$
Tmt-D-Lys-Phe-Arg-NH$_2$
Hmt-D-Lys-Phe-Lys-NH$_2$
Hmt-D-Lys-Phe-Orn-NH$_2$
Hmt-D-Lys-Phe-Dab-NH$_2$
Hmt-D-Lys-Phe-Dap-NH$_2$
Hmt-D-Lys-Phe-Arg-NH$_2$
Mmt-D-Orn-Phe-Arg-NH$_2$
Mmt-D-Dab-Phe-Arg-NH$_2$
Mmt-D-Dap-Phe-Arg-NH$_2$
Mmt-D-Arg-Phe-Arg-NH$_2$
Tmt-D-Orn-Phe-Arg-NH$_2$
Tmt-D-Dab-Phe-Arg-NH$_2$
Tmt-D-Dap-Phe-Arg-NH$_2$
Tmt-D-Arg-Phe-Arg-NH$_2$
Hmt-D-Orn-Phe-Arg-NH$_2$
Hmt-D-Dab-Phe-Arg-NH$_2$
Hmt-D-Dap-Phe-Arg-NH$_2$
Hmt-D-Arg-Phe-Arg-NH$_2$
Lys-Phe-D-Arg-Dmt-NH$_2$
Tyr-D-Arg-Phe-Lys-Cys-NH$_2$
2',6'-Dmt-D-Arg-Phe-Lys-Cys-NH$_2$
2',6'-Dmt-D-Cit-Phe-Lys-Cys-NH$_2$
2',6'-Dmt-D-Arg-2',6'-Dmt-Lys-Cys-NH$_2$
Tyr-D-Lys-Phe-Arg-Cys-NH$_2$
3',5'-Dmt-D-Lys-Phe-Arg-Cys-NH$_2$
D-Arg-Dmt-Lys-Phe-Cys-NH$_2$
D-Arg-Dmt-Lys-Phe-Glu-Cys-Gly-NH$_2$
D-Arg-Dmt-Lys-Phe-Ser-Cys-NH$_2$
D-Arg-Dmt-Lys-Phe-Gly-Cys-NH$_2$
Phe-D-Arg-Phe-Lys-Cys-NH$_2$
Phe-D-Arg-Phe-Lys-Glu-Cys-Gly-NH$_2$
Phe-D-Arg-Phe-Lys-Ser-Cys-NH$_2$
Phe-D-Arg-Phe-Lys-Gly-Cys-NH$_2$
Phe-D-Arg-Dmt-Lys-Cys-NH$_2$
Phe-D-Arg-Dmt-Lys-Glu-Cys-Gly-NH$_2$
Phe-D-Arg-Dmt-Lys-Ser-Cys-NH$_2$
Phe-D-Arg-Dmt-Lys-Gly-Cys-NH$_2$
D-Arg-Dmt-Lys-Trp-NH$_2$
D-Arg-Trp-Lys-Trp-NH$_2$
D-Arg-Dmt-Lys-Phe-Met-NH$_2$
D-Arg-Dmt-Lys(N$^\alpha$Me)-Phe-NH$_2$
D-Arg-Dmt-Lys-Phe(NMe)—NH$_2$
D-Arg-Dmt-Lys(N$^\alpha$Me)-Phe(NMe)—NH$_2$
D-Arg(N$^\alpha$Me)-Dmt-(NMe)-Lys(N$^\alpha$Me)-Phe(NMe)—NH$_2$
D-Arg-Dmt-Lys-Phe-Trp-NH$_2$
D-Arg-Dmt-Lys-Dmt-Lys-Trp-NH$_2$
D-Arg-Dmt-Lys-Phe-Lys-Met-NH$_2$
D-Arg-Dmt-Lys-Dmt-Lys-Met-NH$_2$
D-Arg-Dmt-Lys-Phe-Sar-Gly-Cys-NH$_2$
D-Arg-Ψ[CH$_2$—NH]Dmt-Lys-Phe-NH$_2$
D-Arg-Dmt-Ψ[CH$_2$—NH]Lys-Phe-NH$_2$
D-Arg-Dmt-LysΨ[CH$_2$—NH]Phe-NH$_2$
D-Arg-Dmt-Ψ[CH$_2$—NH]Lys-Ψ[CH$_2$—NH]Phe-NH$_2$
Phe-D-Arg Phe-Lys-Cys-NH$_2$
d$_5$-D-Arg-2',6'-Dmt-Lys-Phe-NH$_2$
Met-Tyr-D-Arg-Phe-Arg-NH$_2$
D-Arg-Dmt-D-Lys-Phe-NH$_2$
D-Arg-Dmt-Lys-D-Phe-NH$_2$
Phe-D-Arg-D-Phe-Lys-NH$_2$
Phe-D-Arg-Phe-D-Lys-NH$_2$
D-Phe-D-Arg-D-Phe-D-Lys-NH$_2$

TABLE 5-continued

Exemplary Aromatic-Cationic Peptides

Lys-D-Phe-Arg-Dmt-NH$_2$
D-Arg-Arg-Dmt-Phe-NH$_2$
Dmt-D-Phe-Arg-Lys-NH$_2$
Phe-D-Dmt-Arg-Lys-NH$_2$
D-Arg-Dmt-Lys-NH$_2$
Arg-D-Dmt-Lys-NH$_2$
D-Arg-Dmt-Phe-NH$_2$
Arg-D-Dmt-Arg-NH$_2$
Dmt-D-Arg-NH$_2$
D-Arg-Dmt-NH$_2$
D-Dmt-Arg-NH$_2$
Arg-D-Dmt-NH$_2$
D-Arg-D-Dmt-NH$_2$
D-Arg-D-Tyr-Lys-Phe-NH$_2$
D-Arg-Tyr-D-Lys-Phe-NH$_2$
D-Arg-Tyr-Lys-D-Phe-NH$_2$
D-Arg-D-Tyr-D-Lys-D-Phe-NH$_2$
Lys-D-Phe-Arg-Tyr-NH$_2$
D-Arg-Arg-Tyr-Phe-NH$_2$
Tyr-D-Phe-Arg-Lys-NH$_2$
Phe-D-Tyr-Arg-Lys-NH$_2$
D-Arg-Tyr-Lys-NH$_2$
Arg-D-Tyr-Lys-NH$_2$
D-Arg-Tyr-Phe-NH$_2$
Arg-D-Tyr-Arg-NH$_2$
Tyr-D-Arg-NH$_2$
D-Arg-Tyr-NH$_2$
D-Tyr-Arg-NH$_2$
Arg-D-Tyr-NH$_2$
D-Arg-D-Tyr-NH$_2$
Dmt-Lys-Phe-NH$_2$
Lys-Dmt-D-Arg-NH$_2$
Phe-Lys-Dmt-NH$_2$
D-Arg-Phe-Lys-NH$_2$
D-Arg-Cha-Lys-NH$_2$
D-Arg-Trp-Lys-NH$_2$
Dmt-Lys-D-Phe-NH$_2$
Dmt-Lys-NH$_2$
Lys-Phe-NH$_2$
D-Arg-Cha-Lys-Cha-NH$_2$
D-Nle-Dmt-Ahe-Phe-NH$_2$
D-Nle-Cha-Ahe-Cha-NH$_2$
6-Butyric acid CoQ0-Phe-D-Arg-Phe-Lys-NH$_2$
6-Decanoic acid CoQ0-Phe-D-Arg-Phe-Lys-NH$_2$
Arg-Arg-Dmt-Phe (SEQ ID NO: 3)
Arg-Cha-Lys
Arg-Dmt
Arg-Dmt-Arg
Arg-Dmt-Lys
Arg-Dmt-Lys-Phe (SEQ ID NO: 4)
Arg-Dmt-Lys-Phe-Cys (SEQ ID NO: 5)
Arg-Dmt-Phe
Arg-Dmt-Phe-Lys (SEQ ID NO: 6)
Arg-Lys-Dmt-Phe (SEQ ID NO: 7)
Arg-Lys-Phe-Dmt (SEQ ID NO: 8)
Arg-Phe-Dmt-Lys (SEQ ID NO: 9)
Arg-Phe-Lys
Arg-Trp-Lys
Arg-Tyr-Lys
Arg-Tyr-Lys-Phe (SEQ ID NO: 10)
D-Arg-D-Dmt-D-Lys-D-Phe-NH$_2$
D-Arg-D-Dmt-D-Lys-Phe-NH$_2$
D-Arg-D-Dmt-Lys-D-Phe-NH$_2$
D-Arg-D-Dmt-Lys-Phe-NH$_2$
D-Arg-Dmt-D-Lys-NH$_2$
D-Arg-Dmt-D-Lys-Phe-NH$_2$
D-Arg-Dmt-Lys-NH$_2$
D-Arg-Dmt-Lys-Phe-Cys
D-Arg-Dmt-D-Lys-D-Phe-NH$_2$
D-Arg-Dmt-Lys-D-Phe-NH$_2$
Dmt-Arg
Dmt-Lys
Dmt-Lys-Phe
Dmt-Phe-Arg-Lys (SEQ ID NO: 11)
H-Arg-D-Dmt-Lys-Phe-NH$_2$
H-Arg-Dmt-Lys-Phe-NH$_2$ (SEQ ID NO: 12)
H-D-Arg-2,6-dichloro-L-tyrosine-Lys-Phe-NH$_2$
H-D-Arg-2,6-dichlorotyrosine-Lys-Phe-NH$_2$
H-D-Arg-2,6-difluoro-L-tyrosine-Lys-Phe-NH$_2$
H-D-Arg-2,6-difluorotyrosine-Lys-Phe-NH$_2$
H-D-Arg-2,6-dimethyl-L-phenylalanine-Lys-Phe-NH$_2$
H-D-Arg-2,6-dimethylphenylalanine-Lys-Phe-NH$_2$
H-D-Arg-4-methoxy-2,6-dimethyl-L-tyrosine-Lys-Phe-NH$_2$
H-D-Arg-4-methoxy-2,6-dimethyltyrosine-Lys-Phe-NH$_2$
H-D-Arg-Arg-Dmt-Phe-NH$_2$
H-D-Arg-Dmt-Lys-2,6-dimethylphenylalanine-NH$_2$
H-D-Arg-Dmt-Lys-3-hydroxyphenylalanine-NH$_2$
H-D-Arg-Dmt-Lys-OH
H-D-Arg-Dmt-Lys-Phe-OH
H-D-Arg-Dmt-N6-acetyllysine-Phe-NH$_2$
H-D-Arg-Dmt-OH
H-D-Arg-D-Phe-Lys-Phe-NH$_2$
H-D-Arg-D-Trp-Lys-Phe-NH$_2$
H-D-Arg-Dmt-Lys-2,6-dimethyl-L-phenylalanine-NH$_2$
H-D-Arg-Dmt-Lys-3-hydroxy-L-phenylalanine-NH$_2$
H-D-Arg-Dmt-Lys-D-Dmt-NH$_2$
H-D-Arg-Dmt-Lys-D-Trp-NH$_2$
H-D-Arg-Dmt-Lys-D-Tyr-NH$_2$
H-D-Arg-Dmt-Lys-Dmt-NH$_2$
H-D-Arg-Dmt-Lys-Tyr-NH$_2$
H-D-Arg-Dmt-N6-acetyl-Lys-Phe-NH$_2$
H-D-Arg-Lys-Phe-Dmt-NH$_2$
H-D-Arg-Phe-Lys-Dmt-NH$_2$
H-D-Arg-Phe-Lys-Phe-NH$_2$
H-D-Arg-Tyr-Lys-Phe-NH$_2$
H-D-His-Dmt-Lys-Phe-NH$_2$
H-D-Lys-Dmt-Lys-Phe-NH$_2$
H-Dmt-D-Arg-Lys-Phe-NH$_2$
H-Dmt-D-Arg-Phe-Lys-NH$_2$
H-Dmt-D-Phe-Arg-Lys-NH$_2$
H-Dmt-Lys-D-Arg-Phe-NH$_2$
H-Dmt-Lys-Phe-D-Arg-NH$_2$
H-Dmt-Phe-D-Arg-Lys-NH$_2$
H-Dmt-Phe-Lys-D-Arg-NH$_2$
H-D-N2-acetylarginine-Dmt-Lys-Phe-NH$_2$
H-D-N8-acetylarginine-Dmt-Lys-Phe-NH$_2$
H-Dmt-D-Arg-Lys-Phe-NH$_2$
H-Dmt-Lys-D-Arg-Phe-NH$_2$
H-His-Dmt-Lys-Phe-NH$_2$ (SEQ ID NO: 13)
H-Lys-D-Arg-Dmt-Phe-NH$_2$
H-Lys-Dmt-Lys-Phe-NH$_2$ (SEQ ID NO: 14)
H-Phe-D-Arg-Dmt-Lys-NH$_2$
H-Phe-D-Arg-Lys-Dmt-NH$_2$
H-Phe-Dmt-D-Arg-Lys-NH$_2$
H-Phe-Dmt-Lys-D-Arg-NH$_2$
H-Phe-Lys-Dmt-D-Arg-NH$_2$
H-N2-acetyl-D-arginine-Dmt-Lys-Phe-NH$_2$
H-N7-acetyl-D-arginine-Dmt-Lys-Phe-NH$_2$
H-Phe(d5)-D-Arg-Phe(d5)-Lys-NH$_2$
H-Phe-Arg-Phe-Lys-NH$_2$ (SEQ ID NO: 15)
H-Phe-D-Arg-Phe-D-Lys-NH$_2$
H-Phe-D-Arg-Phe-Lys-Glu-Cys-Gly-NH$_2$
Arg-D-Dmt-D-Lys-D-Phe-NH$_2$
Arg-D-Dmt-D-Lys-Phe-NH$_2$
Arg-D-Dmt-Lys-D-Phe-NH$_2$
Arg-Dmt-D-Lys-D-Phe-NH$_2$
Arg-Dmt-D-Lys-Phe-NH$_2$
Arg-Dmt-Lys-D-Phe-NH$_2$
Lys-Dmt-Arf
Lys-Phe
Lys-Phe-Arg-Dmt (SEQ ID NO: 16)
Lys-Trp-Arg
Lys-Trp-D-Arg-NH$_2$
Phe-Arg-Dmt-Lys (SEQ ID NO: 17)
Phe-Arg-Phe-Lys (SEQ ID NO: 18)
Phe-Arg-Lys-Glu-Cys-Gly (SEQ ID NO: 19)
Phe-Dmt-Arg-Lys (SEQ ID NO: 20)
Phe-Lys-Dmt
Succinic monoester CoQ0-Phe-D-Arg-Phe-Lys-NH$_2$
H-Phe(d$_5$)-D-Arg-Phe(d$_5$)-Lys-NH$_2$
D-Arg-D-Tyr-D-Lys-D-Phe-NH$_2$ (P-231D)
Tyr-Arg-Phe-Lys-Glu-His-Trp-D-Arg TABLE 5-continued Exemplary Aromatic-Cationic Peptides Lys-Gln-Tyr-D-Arg-Phe-Trp
Dox-Succ-D-Arg-L-2',6'-Dimethyl-Tyr-L-Lys(Dox-Succ)-L-Phe-NH$_2$
D-Arg-Dmt-Lys-Dox-Phe-NH-Dox Ald = β-(6'-dimethylamino-2'-naphthoyl)alanine
atnDap = β-anthraniloyl-L-α,β-diaminopropionic acid
Bio = biotin
Cha = cyclohexyl
d$_5$ = deuteriums
Dab = diaminobutyric
Dap = diaminopropionic acid
Dmp = dimethylphenylalanine
Dmt = dimethyltyrosine
dnsDap = β-dansyl-L-α,β-diaminopropionic acid
Hmt = 2'-hydroxy,6'-methyltyrosine
Mmt = 2'-methyltyrosine
Tmt = N,2',6'-trimethyltyrosine In one embodiment, the peptides have mu-opioid receptor agonist activity (i.e., they activate the mu-opioid receptor). Peptides which have mu-opioid receptor agonist activity are typically those peptides which have a tyrosine residue or a tyrosine derivative at the N-terminus (i.e., the first amino acid position). Suitable derivatives of tyrosine include 2'-methyltyrosine (Mmt); 2',6'-dimethyltyrosine (2'6'-Dmt); 3',5'-dimethyltyrosine (3'5'Dmt); N,2',6'-trimethyltyrosine (Tmt); and 2'-hydroxy-6'-methyltyrosine (Hmt).

In one embodiment, a peptide that has mu-opioid receptor agonist activity has the formula Tyr-D-Arg-Phe-Lys-NH$_2$. Tyr-D-Arg-Phe-Lys-NH$_2$ has a net positive charge of three, contributed by the amino acids tyrosine, arginine, and lysine and has two aromatic groups contributed by the amino acids phenylalanine and tyrosine. The tyrosine of Tyr-D-Arg-Phe-Lys-NH$_2$ can be a modified derivative of tyrosine such as in 2',6'-dimethyltyrosine to produce the compound having the formula 2',6'-Dmt-D-Arg-Phe-Lys-NH$_2$. 2',6'-Dmt-D-Arg-Phe-Lys-NH$_2$ has a molecular weight of 640 and carries a net three positive charge at physiological pH. 2',6'-Dmt-D-Arg-Phe-Lys-NH$_2$ readily penetrates the plasma membrane of several mammalian cell types in an energy-independent manner (Zhao et al., *J. Pharmacol Exp Ther.*, 304:425-432, 2003).

Alternatively, in other instances, the aromatic-cationic peptide does not have mu-opioid receptor agonist activity. For example, during long-term treatment, such as in a chronic disease state or condition, the use of an aromatic-cationic peptide that activates the mu-opioid receptor may be contraindicated. In these instances, the potentially adverse or addictive effects of the aromatic-cationic peptide may preclude the use of an aromatic-cationic peptide that activates the mu-opioid receptor in the treatment regimen of a human patient or other mammal. Potential adverse effects may include sedation, constipation and respiratory depression. In such instances an aromatic-cationic peptide that does not activate the mu-opioid receptor may be an appropriate treatment. Peptides that do not have mu-opioid receptor agonist activity generally do not have a tyrosine residue or a derivative of tyrosine at the N-terminus (i.e., amino acid position 1). The amino acid at the N-terminus can be any naturally occurring or non-naturally occurring amino acid other than tyrosine. In one embodiment, the amino acid at the N-terminus is phenylalanine or its derivative. Exemplary derivatives of phenylalanine include 2'-methylphenylalanine (Mmp), 2',6'-dimethylphenylalanine (2',6'-Dmp), N,2',6'-trimethylphenylalanine (Tmp), and 2'-hydroxy-6'-methylphenylalanine (Hmp).

An example of an aromatic-cationic peptide that does not have mu-opioid receptor agonist activity has the formula Phe-D-Arg-Phe-Lys-NH$_2$. Alternatively, the N-terminal phenylalanine can be a derivative of phenylalanine such as 2',6'-dimethylphenylalanine (2'6'-Dmp). In one embodiment, the amino acid sequence of 2',6'-Dmt-D-Arg-Phe-Lys-NH$_2$ is rearranged such that Dmt is not at the N-terminus. An example of such an aromatic-cationic peptide that does not have mu-opioid receptor agonist activity has the formula D-Arg-2'6'-Dmt-Lys-Phe-NH$_2$.

Suitable substitution variants of the peptides listed herein include conservative amino acid substitutions. Amino acids may be grouped according to their physicochemical characteristics as follows:

(a) Non-polar amino acids: Ala (A) Ser (S) Thr (T) Pro (P) Gly (G) Cys (C);
(b) Acidic amino acids: Asn (N) Asp (D) Glu (E) Gln (Q);
(c) Basic amino acids: His (H) Arg (R) Lys (K);
(d) Hydrophobic amino acids: Met (M) Leu (L) Ile (I) Val (V); and
(e) Aromatic amino acids: Phe (F) Tyr (Y) Trp (W) His (H).

Substitutions of an amino acid in a peptide by another amino acid in the same group are referred to as a conservative substitution and may preserve the physicochemical characteristics of the original peptide. In contrast, substitutions of an amino acid in a peptide by another amino acid in a different group are generally more likely to alter the characteristics of the original peptide.

Examples of peptides that activate mu-opioid receptors include, but are not limited to, the aromatic-cationic peptides shown in Table 6.

TABLE 6

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Tyr | D-Arg | Phe | Lys | NH$_2$ |
| Tyr | D-Arg | Phe | Orn | NH$_2$ |
| Tyr | D-Arg | Phe | Dab | NH$_2$ |
| Tyr | D-Arg | Phe | Dap | NH$_2$ |
| 2'6'Dmt | D-Arg | Phe | Lys | NH$_2$ |
| 2'6'Dmt | D-Arg | Phe | Lys-NH(CH$_2$)$_2$—NH-dns | NH$_2$ |
| 2'6'Dmt | D-Arg | Phe | Lys-NH(CH$_2$)$_2$—NH-atn | NH$_2$ |
| 2'6'Dmt | D-Arg | Phe | dnsLys | NH$_2$ |
| 2'6'Dmt | D-Cit | Phe | Lys | NH$_2$ |
| 2'6'Dmt | D-Cit | Phe | Ahp | NH$_2$ |
| 2'6'Dmt | D-Arg | Phe | Orn | NH$_2$ |
| 2'6'Dmt | D-Arg | Phe | Dab | NH$_2$ |
| 2'6'Dmt | D-Arg | Phe | Dap | NH$_2$ |
| 2'6'Dmt | D-Arg | Phe | Ahp(2-aminoheptanoic acid) | NH$_2$ |
| Bio-2'6'Dmt | D-Arg | Phe | Lys | NH$_2$ |
| 3'5'Dmt | D-Arg | Phe | Lys | NH$_2$ |
| 3'5'Dmt | D-Arg | Phe | Orn | NH$_2$ |
| 3'5'Dmt | D-Arg | Phe | Dab | NH$_2$ |
| 3'5'Dmt | D-Arg | Phe | Dap | NH$_2$ |
| Tyr | D-Arg | Tyr | Lys | NH$_2$ |
| Tyr | D-Arg | Tyr | Orn | NH$_2$ |
| Tyr | D-Arg | Tyr | Dab | NH$_2$ |
| Tyr | D-Arg | Tyr | Dap | NH$_2$ |
| 2'6'Dmt | D-Arg | Tyr | Lys | NH$_2$ |
| 2'6'Dmt | D-Arg | Tyr | Orn | NH$_2$ |
| 2'6'Dmt | D-Arg | Tyr | Dab | NH$_2$ |
| 2'6'Dmt | D-Arg | Tyr | Dap | NH$_2$ |
| 2'6'Dmt | D-Arg | 2'6'Dmt | Lys | NH$_2$ |
| 2'6'Dmt | D-Arg | 2'6'Dmt | Orn | NH$_2$ |
| 2'6'Dmt | D-Arg | 2'6'Dmt | Dab | NH$_2$ |

TABLE 6-continued

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| 2'6'Dmt | D-Arg | 2'6'Dmt | Dap | NH$_2$ |
| 3'5'Dmt | D-Arg | 3'5'Dmt | Arg | NH$_2$ |
| 3'5'Dmt | D-Arg | 3'5'Dmt | Lys | NH$_2$ |
| 3'5'Dmt | D-Arg | 3'5'Dmt | Orn | NH$_2$ |
| 3'5'Dmt | D-Arg | 3'5'Dmt | Dab | NH$_2$ |
| Tyr | D-Lys | Phe | Dap | NH$_2$ |
| Tyr | D-Lys | Phe | Arg | NH$_2$ |
| Tyr | D-Lys | Phe | Lys | NH$_2$ |
| Tyr | D-Lys | Phe | Orn | NH$_2$ |
| 2'6'Dmt | D-Lys | Phe | Dab | NH$_2$ |
| 2'6'Dmt | D-Lys | Phe | Dap | NH$_2$ |
| 2'6'Dmt | D-Lys | Phe | Arg | NH$_2$ |
| 2'6'Dmt | D-Lys | Phe | Lys | NH$_2$ |
| 3'5'Dmt | D-Lys | Phe | Orn | NH$_2$ |
| 3'5'Dmt | D-Lys | Phe | Dab | NH$_2$ |
| 3'5'Dmt | D-Lys | Phe | Dap | NH$_2$ |
| 3'5'Dmt | D-Lys | Phe | Arg | NH$_2$ |
| Tyr | D-Lys | Tyr | Lys | NH$_2$ |
| Tyr | D-Lys | Tyr | Orn | NH$_2$ |
| Tyr | D-Lys | Tyr | Dab | NH$_2$ |
| Tyr | D-Lys | Tyr | Dap | NH$_2$ |
| 2'6'Dmt | D-Lys | Tyr | Lys | NH$_2$ |
| 2'6'Dmt | D-Lys | Tyr | Orn | NH$_2$ |
| 2'6'Dmt | D-Lys | Tyr | Dab | NH$_2$ |
| 2'6'Dmt | D-Lys | Tyr | Dap | NH$_2$ |
| 2'6'Dmt | D-Lys | 2'6'Dmt | Lys | NH$_2$ |
| 2'6'Dmt | D-Lys | 2'6'Dmt | Orn | NH$_2$ |
| 2'6'Dmt | D-Lys | 2'6'Dmt | Dab | NH$_2$ |
| 2'6'Dmt | D-Lys | 2'6'Dmt | Dap | NH$_2$ |
| 2'6'Dmt | D-Arg | Phe | dnsDap | NH$_2$ |
| 2'6'Dmt | D-Arg | Phe | atnDap | NH$_2$ |
| 3'5'Dmt | D-Lys | 3'5'Dmt | Lys | NH$_2$ |
| 3'5'Dmt | D-Lys | 3'5'Dmt | Orn | NH$_2$ |
| 3'5'Dmt | D-Lys | 3'5'Dmt | Dab | NH$_2$ |
| 3'5'Dmt | D-Lys | 3'5'Dmt | Dap | NH$_2$ |
| Tyr | D-Lys | Phe | Arg | NH$_2$ |
| Tyr | D-Orn | Phe | Arg | NH$_2$ |
| Tyr | D-Dab | Phe | Arg | NH$_2$ |
| Tyr | D-Dap | Phe | Arg | NH$_2$ |
| 2'6'Dmt | D-Arg | Phe | Arg | NH$_2$ |
| 2'6'Dmt | D-Lys | Phe | Arg | NH$_2$ |
| 2'6'Dmt | D-Orn | Phe | Arg | NH$_2$ |
| 2'6'Dmt | D-Dab | Phe | Arg | NH$_2$ |
| 3'5'Dmt | D-Dap | Phe | Arg | NH$_2$ |
| 3'5'Dmt | D-Arg | Phe | Arg | NH$_2$ |
| 3'5'Dmt | D-Lys | Phe | Arg | NH$_2$ |
| 3'5'Dmt | D-Orn | Phe | Arg | NH$_2$ |
| Tyr | D-Lys | Tyr | Arg | NH$_2$ |
| Tyr | D-Orn | Tyr | Arg | NH$_2$ |
| Tyr | D-Dab | Tyr | Arg | NH$_2$ |
| Tyr | D-Dap | Tyr | Arg | NH$_2$ |
| 2'6'Dmt | D-Arg | 2'6'Dmt | Arg | NH$_2$ |
| 2'6'Dmt | D-Lys | 2'6'Dmt | Arg | NH$_2$ |
| 2'6'Dmt | D-Orn | 2'6'Dmt | Arg | NH$_2$ |
| 2'6'Dmt | D-Dab | 2'6'Dmt | Arg | NH$_2$ |
| 3'5'Dmt | D-Dap | 3'5'Dmt | Arg | NH$_2$ |
| 3'5'Dmt | D-Arg | 3'5'Dmt | Arg | NH$_2$ |
| 3'5'Dmt | D-Lys | 3'5'Dmt | Arg | NH$_2$ |
| 3'5'Dmt | D-Orn | 3'5'Dmt | Arg | NH$_2$ |
| Mmt | D-Arg | Phe | Lys | NH$_2$ |
| Mmt | D-Arg | Phe | Orn | NH$_2$ |
| Mmt | D-Arg | Phe | Dab | NH$_2$ |
| Mmt | D-Arg | Phe | Dap | NH$_2$ |
| Tmt | D-Arg | Phe | Lys | NH$_2$ |
| Tmt | D-Arg | Phe | Orn | NH$_2$ |
| Tmt | D-Arg | Phe | Dab | NH$_2$ |
| Tmt | D-Arg | Phe | Dap | NH$_2$ |
| Hmt | D-Arg | Phe | Lys | NH$_2$ |
| Hmt | D-Arg | Phe | Orn | NH$_2$ |
| Hmt | D-Arg | Phe | Dab | NH$_2$ |
| Hmt | D-Arg | Phe | Dap | NH$_2$ |
| Mmt | D-Lys | Phe | Lys | NH$_2$ |
| Mmt | D-Lys | Phe | Orn | NH$_2$ |
| Mmt | D-Lys | Phe | Dab | NH$_2$ |
| Mmt | D-Lys | Phe | Dap | NH$_2$ |
| Mmt | D-Lys | Phe | Arg | NH$_2$ |
| Tmt | D-Lys | Phe | Lys | NH$_2$ |
| Tmt | D-Lys | Phe | Orn | NH$_2$ |
| Tmt | D-Lys | Phe | Dab | NH$_2$ |
| Tmt | D-Lys | Phe | Dap | NH$_2$ |
| Tmt | D-Lys | Phe | Arg | NH$_2$ |
| Hmt | D-Lys | Phe | Lys | NH$_2$ |
| Hmt | D-Lys | Phe | Orn | NH$_2$ |
| Hmt | D-Lys | Phe | Dab | NH$_2$ |
| Hmt | D-Lys | Phe | Dap | NH$_2$ |
| Hmt | D-Lys | Phe | Arg | NH$_2$ |
| Mmt | D-Lys | Phe | Arg | NH$_2$ |
| Mmt | D-Orn | Phe | Arg | NH$_2$ |
| Mmt | D-Dab | Phe | Arg | NH$_2$ |
| Mmt | D-Dap | Phe | Arg | NH$_2$ |
| Mmt | D-Arg | Phe | Arg | NH$_2$ |
| Tmt | D-Lys | Phe | Arg | NH$_2$ |
| Tmt | D-Orn | Phe | Arg | NH$_2$ |
| Tmt | D-Dab | Phe | Arg | NH$_2$ |
| Tmt | D-Dap | Phe | Arg | NH$_2$ |
| Tmt | D-Arg | Phe | Arg | NH$_2$ |
| Hmt | D-Lys | Phe | Arg | NH$_2$ |
| Hmt | D-Orn | Phe | Arg | NH$_2$ |
| Hmt | D-Dab | Phe | Arg | NH$_2$ |
| Hmt | D-Dap | Phe | Arg | NH$_2$ |
| Hmt | D-Arg | Phe | Arg | NH$_2$ |

Dab = diaminobutyric
Dap = diaminopropionic acid
Dmt = dimethyltyrosine
Mmt = 2'-methyltyrosine
Tmt = N,2',6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin Examples of peptides that do not activate mu-opioid receptors include, but are not limited to, the aromatic-cationic peptides shown in Table 7.

TABLE 7

Peptide Analogs Lacking Mu-Opioid Activity

| Amino Acid Position 1 | Amino Acid Position 2 | Amino Acid Position 3 | Amino Acid Position 4 | C-Terminal Modification |
|---|---|---|---|---|
| D-Arg | Dmt | Lys | Phe | NH$_2$ |
| D-Arg | Dmt | Phe | Lys | NH$_2$ |
| D-Arg | Phe | Lys | Dmt | NH$_2$ |
| D-Arg | Phe | Dmt | Lys | NH$_2$ |
| D-Arg | Lys | Dmt | Phe | NH$_2$ |
| D-Arg | Lys | Phe | Dmt | NH$_2$ |
| Phe | Lys | Dmt | D-Arg | NH$_2$ |
| Phe | Lys | D-Arg | Dmt | NH$_2$ |
| Phe | D-Arg | Phe | Lys | NH$_2$ |
| Phe | D-Arg | Dmt | Lys | NH$_2$ |
| Phe | D-Arg | Lys | Dmt | NH$_2$ |
| Phe | Dmt | D-Arg | Lys | NH$_2$ |
| Phe | Dmt | Lys | D-Arg | NH$_2$ |
| Lys | Phe | D-Arg | Dmt | NH$_2$ |
| Lys | Phe | Dmt | D-Arg | NH$_2$ |
| Lys | Dmt | D-Arg | Phe | NH$_2$ |
| Lys | Dmt | Phe | D-Arg | NH$_2$ |
| Lys | D-Arg | Phe | Dmt | NH$_2$ |
| Lys | D-Arg | Dmt | Phe | NH$_2$ |
| D-Arg | Dmt | D-Arg | Phe | NH$_2$ |

TABLE 7-continued

Peptide Analogs Lacking Mu-Opioid Activity

| Amino Acid Position 1 | Amino Acid Position 2 | Amino Acid Position 3 | Amino Acid Position 4 | C-Terminal Modification |
|---|---|---|---|---|
| D-Arg | Dmt | D-Arg | Dmt | $NH_2$ |
| D-Arg | Dmt | D-Arg | Tyr | $NH_2$ |
| D-Arg | Dmt | D-Arg | Trp | $NH_2$ |
| Trp | D-Arg | Phe | Lys | $NH_2$ |
| Trp | D-Arg | Tyr | Lys | $NH_2$ |
| Trp | D-Arg | Trp | Lys | $NH_2$ |
| Trp | D-Arg | Dmt | Lys | $NH_2$ |
| D-Arg | Trp | Lys | Phe | $NH_2$ |
| D-Arg | Trp | Phe | Lys | $NH_2$ |
| D-Arg | Trp | Lys | Dmt | $NH_2$ |
| D-Arg | Trp | Dmt | Lys | $NH_2$ |
| D-Arg | Lys | Trp | Phe | $NH_2$ |
| D-Arg | Lys | Trp | Dmt | $NH_2$ |
| Cha | D-Arg | Phe | Lys | $NH_2$ |
| Ala | D-Arg | Phe | Lys | $NH_2$ |

Cha = cyclohexyl alanine

The amino acids of the peptides shown in Table 6 and 7 may be in either the L- or the D-configuration.

The peptides may be synthesized by any of the methods well known in the art. Suitable methods for chemically synthesizing the protein include, for example, those described by Stuart and Young in *Solid Phase Peptide Synthesis*, Second Edition, Pierce Chemical Company (1984), and in *Methods Enzymol.*, 289, Academic Press, Inc., New York (1997).

In practicing the present technology, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.* (Academic Press, Inc., 1984); *Gene Transfer Vectors for Mammalian Cells*, Miller & Calos, Eds. (Cold Spring Harbor Laboratory, N Y, 1987); and *Meth. Enzymol.*, Vols. 154 and 155, Wu & Grossman, and Wu, Eds., respectively.

Use of the Aromatic-Cationic Peptides to Prevent, Ameliorate, or Treat Vitiligo

General.

In some embodiments, the methods disclosed herein provide therapies for the prevention, amelioration or treatment of vitiligo and/or symptoms of vitiligo comprising administering an effective amount of an aromatic-cationic peptide or a pharmaceutically acceptable salt thereof, such as acetate, tartrate salt, or trifluoroacetate salt. Thus, for example, one or more aromatic-cationic peptides may be: (1) co-formulated and administered or delivered alone or simultaneously in a combined formulation with other active agents or aromatic-cationic peptides; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used. Administering such combinations of aromatic peptides and other active agents can result in synergistic biological effect when administered in a therapeutically effective amount to a subject suffering from a medical disease or condition and in need of treatment. An advantage of such an approach is that lower doses of aromatic-cationic peptide and/or other active agents may be needed to prevent, ameliorate or treat vitiligo in a subject. Further, potential side effects of treatment may be avoided by use of lower dosages of aromatic-cationic peptide and/or other active agents.

The aromatic-cationic peptides described herein, such as D-Arg-2',6'-Dmt-Lys-Phe-$NH_2$, or pharmaceutically acceptable salts thereof, such as acetate salt, tartrate salt, or trifluoroacetate salt, are useful to prevent or treat disease. Specifically, the disclosure provides for both prophylactic and therapeutic methods of treating a subject having or suspected of having vitiligo. For example, in some embodiments, the disclosure provides for both prophylactic and therapeutic methods of treating a subject exhibiting melanocyte degeneration caused by a gene mutation in NLRP1 or TYR. Accordingly, the present methods provide for the prevention and/or treatment of vitiligo in a subject by administering an effective amount of an aromatic-cationic peptide to a subject in need thereof to reduce melanocyte degeneration in the subject. In some embodiments, the present technology relates to the treatment, amelioration or prevention of vitiligo in mammals through administration of therapeutically effective amounts of aromatic-cationic peptides as disclosed herein, such as D-Arg-2',6'-Dmt-Lys-Phe-$NH_2$, or pharmaceutically acceptable salts thereof, such as acetate salt, tartrate salt, or trifluoroacetate salt, to subjects in need thereof.

Prophylactic and Therapeutic Uses of Peptide Conjugates

In some embodiments, at least one aromatic-cationic peptide, such as D-Arg-2',6'-Dmt-Lys-Phe-$NH_2$, or a pharmaceutically acceptable salt thereof, such as acetate, tartrate salt, or trifluoroacetate salt, described herein are useful for preventing or treating vitiligo. Specifically, the disclosure provides for both prophylactic and therapeutic methods of treating a subject suffering from, at risk of, or susceptible to vitiligo. Accordingly, the present methods provide for the prevention and/or treatment of vitiligo in a subject by administering an effective amount of at least one aromatic peptide, such as D-Arg-2',6'-Dmt-Lys-Phe-$NH_2$, or a pharmaceutically acceptable salt thereof, such as acetate, tartrate salt, or trifluoroacetate salt, to a subject in need thereof. In some embodiments, a subject is administered at least one aromatic-cationic peptide in an effort to prevent, treat, or ameliorate vitiligo.

In some embodiments, administration of an effective amount of at least one aromatic-cationic peptide, such as D-Arg-2',6'-Dmt-Lys-Phe-$NH_2$, or a pharmaceutically acceptable salt thereof, such as acetate, tartrate salt, or trifluoroacetate salt, alleviates or eliminates one or more symptom of vitiligo in a subject for therapeutic purposes. In therapeutic applications, compositions or medicaments are administered to a subject suspected of, or already suffering from vitiligo in an amount sufficient to cure, or at least partially arrest, the symptoms of the vitiligo, including its complications and intermediate pathological phenotypes in development of the disease. In some embodiments, administration of an effective amount of at least one aromatic-cationic peptide, such as D-Arg-2',6'-Dmt-Lys-Phe-NH$_2$, or a pharmaceutically acceptable salt thereof, such as acetate, tartrate salt, or trifluoroacetate salt, to a subject modulates one or more signs or symptoms of vitiligo. By way of example, but not by way of limitation, signs and symptoms of vitiligo include, but are not limited to, production of milky-white patches (depigmentation) on the skin (e.g., skin on the face, neck, hands, arms, feet, knees, genitalia, and lips), premature whitening or graying of hair (e.g., on scalp, eyelashes, eyebrow, or beard), loss of color in the tissues that line the inside of the mouth, and loss or change of color of the inner layer of the retina. As such, the disclosure provides methods of treating an individual afflicted with vitiligo. Subjects suffering from vitiligo can be identified by, e.g., any diagnostic or prognostic assays known in the art.

In prophylactic applications, pharmaceutical compositions or medicaments of the an effective amount of at least one aromatic-cationic peptide, such as D-Arg-2',6'-Dmt-Lys-Phe-NH$_2$, or a pharmaceutically acceptable salt thereof, such as acetate, tartrate salt, or trifluoroacetate salt, are administered to a subject susceptible to, or otherwise at risk of a disease or condition in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. Subjects at risk for vitiligo can be identified by, e.g., any diagnostic or prognostic assays known in the art. In some embodiments, administration of at least one aromatic-cationic peptide, such as D-Arg-2',6'-Dmt-Lys-Phe-NH$_2$, or a pharmaceutically acceptable salt thereof, such as acetate, tartrate salt, or trifluoroacetate salt, occurs prior to the manifestation of symptoms characteristic of the aberrancy, such that a disease or disorder is prevented or, alternatively, delayed in its progression. The appropriate compound can be determined based on screening assays described herein.

Determination of the Biological Effect of the Aromatic-Cationic Peptides of the Present Technology.

In various embodiments, suitable in vitro or in vivo assays are performed to determine the effect of a specific aromatic-cationic peptide-based therapeutic and whether its administration is indicated for treatment. In various embodiments, in vitro assays can be performed with representative animal models, to determine if a given aromatic-cationic peptide-based therapeutic exerts the desired effect in reducing melanocyte degeneration, such as decreasing T-cell accumulation and/or cytotoxic killing of melanocytes. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

In some embodiments, melanocyte degeneration is determined by assays well known in the art. In some embodiments, melanocyte degeneration is determined by assays that measure cytotoxicity after epidermal cells are exposed to 100 or 250 μM of 4-tertiary butyl phenol (4-TBP), a common inducer of vitiligo. In some embodiments, melanocyte degeneration is determined by assays that measure the survival rate of epidermal cells that have been exposed to 100 or 250 μM of 4-TBP.

In some embodiments, melanocyte degeneration is determined by assays that measure melanocyte antigen-specific T cell accumulation and cytotoxic activity in autologous skin explants. For a detailed description of the autologous skin explant model, see Van Den Boom et al., *Journal of Investigative Dermatology*, 129: 2220-2232 (2009).

In some embodiments, melanocyte degeneration is determined by assays that measure the progressive depigmentation in the pelage of the vitiligo mouse model before and two weeks after plucking dorsal hairs. In some embodiments, melanocyte degeneration is determined by assays that measure the presence of ocular pigmentation in vitiligo mice. In some embodiments, melanocyte degeneration is determined by assays that measure the contact sensitivity of vitiligo mice to dinitrochlorobenzene. For a detailed description of the vitiligo mouse model, see Lerner et al., *Journal of Investigative Dermatology*, 87(3): 299-304 (1986).

In some embodiments, melanocyte degeneration is determined by assays that measure epidermal depigmentation in an adoptive transfer mouse model of vitiligo. In some embodiments, melanocyte degeneration is determined by assays that measure tyrosinase RNA expression in an adoptive transfer mouse model of vitiligo. For a detailed description of the adoptive transfer mouse model of vitiligo, see Harris et al., *Journal of Investigative Dermatology*, 132: 1869-1876 (2012).

Accordingly, in some embodiments, therapeutic and/or prophylactic treatment of subjects having vitiligo, with an aromatic-cationic peptide as disclosed herein, such as D-Arg-2'6'Dmt-Lys-Phe-NH$_2$ (SS-31) or a pharmaceutically acceptable salt thereof, such as acetate, tartrate salt, or trifluoroacetate salt, will reduce melanocyte degeneration, thereby ameliorating symptoms of vitiligo. Symptoms of vitiligo include, but are not limited to, increased photosensitivity, decreased contact sensitivity response to dinitrochlorobenzene, depigmentation of the skin, mucous membranes, retina, or genitals, and premature whitening or graying of hair on the scalp, eyelashes, eyebrows or beard.

Modes of Administration and Effective Dosages

Any method known to those in the art for contacting a cell, organ or tissue with a peptide may be employed. Suitable methods include in vitro, ex vivo, or in vivo methods. In vivo methods typically include the administration of an aromatic-cationic peptide, such as those described above, to a mammal, suitably a human. When used in vivo for therapy, the aromatic-cationic peptides are administered to the subject in effective amounts (i.e., amounts that have desired therapeutic effect). The dose and dosage regimen will depend upon the degree of the infection in the subject, the characteristics of the particular aromatic-cationic peptide used, e.g., its therapeutic index, the subject, and the subject's history.

The effective amount may be determined during preclinical trials and clinical trials by methods familiar to physicians and clinicians. An effective amount of a peptide useful in the methods may be administered to a mammal in need thereof by any of a number of well-known methods for administering pharmaceutical compounds. The peptide may be administered systemically or locally.

The peptide may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucuronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the salt is an acetate, tartrate salt, or trifluoroacetate salt.

The aromatic-cationic peptides of the present technology described herein can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The aromatic-cationic peptide compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, isotonic agents are included, for example, sugars, polyalcohols such as mannitol, sorbitol, or sodium chloride in the composition. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the aromatic-cationic peptides of the present technology can be delivered in the form of an aerosol spray from a pressurized container or dispenser which contains a suitable propellant, e.g., a gas such as carbon dioxide, or a nebulizer. Such methods include those described in U.S. Pat. No. 6,468,798.

Systemic administration of an aromatic-cationic peptide of the present technology as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

An aromatic-cationic peptide of the present technology can be formulated in a carrier system. The carrier can be a colloidal system. The colloidal system can be a liposome, a phospholipid bilayer vehicle. In one embodiment, the therapeutic peptide is encapsulated in a liposome while maintaining peptide integrity. As one skilled in the art would appreciate, there are a variety of methods to prepare liposomes. (See Lichtenberg et al., *Methods Biochem. Anal.*, 33:337-462 (1988); Anselem et al., *Liposome Technology*, CRC Press (1993)). Liposomal formulations can delay clearance and increase cellular uptake (See Reddy, *Ann. Pharmacother.*, 34(7-8):915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the aromatic-cationic peptide of the present technology can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34(7-8):915-923 (2000)). A polymer formulation for human growth hormone (hGH) has been used in clinical trials. (See Kozarich and Rich, *Chemical Biology*, 2:548-552 (1998)).

Examples of polymer microsphere sustained release formulations are described in PCT publication WO 99/15154 (Tracy et al.), U.S. Pat. Nos. 5,674,534 and 5,716,644 (both to Zale et al.), PCT publication WO 96/40073 (Zale et al.), and PCT publication WO 00/38651 (Shah et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the aromatic-cationic peptides of the present technology are prepared with carriers that will protect the aromatic-cationic peptides of the present technology against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The aromatic-cationic peptides of the present technology can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods*, 4(3):201-9 (1994); and Gregoriadis, "Engineering Liposomes for Drug Delivery: Progress and Problems," *Trends Biotechnol.*, 13(12):527-37 (1995). Mizguchi et al., *Cancer Lett.*, 100:63-69 (1996), describes the use of fusogenic liposomes to deliver a protein to cells both in vivo and in vitro.

Dosage, toxicity and therapeutic efficacy of the aromatic-cationic peptide of the present technology can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In some embodiments, the aromatic-cationic peptide of the present technology exhibit high therapeutic indices. While aromatic-cationic peptides of the present technology that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies within a range of circulating concentrations that include the ED50 with little or no toxicity. The dosage may vary within this range depending upon the dosage form employed and the route of administration utilized. For any aromatic-cationic peptide of the present technology used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the aromatic-cationic peptides of the present technology, sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of peptide ranges from 0.001-10,000 micrograms per kg body weight. In one embodiment, aromatic-cationic peptide concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, and until the subject shows partial or complete amelioration of symptoms of disease. Thereafter, the patient can be administered a prophylactic regime.

In some embodiments, a therapeutically effective amount of an aromatic-cationic peptide of the present technology may be defined as a concentration of peptide at the target tissue of $10^{-12}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue. In some embodiments, the doses are administered by single daily or weekly administration, but may also include continuous administration (e.g., parenteral infusion or transdermal application). In some embodiments, the dosage of the aromatic-cationic peptide of the present technology is provided at a "low," "mid," or "high" dose level. In one embodiment, the low dose is provided from about 0.0001 to about 0.5 mg/kg/h, suitably from about 0.001 to about 0.1 mg/kg/h. In one embodiment, the mid-dose is provided from about 0.01 to about 1.0 mg/kg/h, suitably from about 0.01 to about 0.5 mg/kg/h. In one embodiment, the high dose is provided from about 0.5 to about 10 mg/kg/h, suitably from about 0.5 to about 2 mg/kg/h.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance present methods can be any mammal, including, for example, farm animals, such as sheep, pigs, cows, and horses; pet animals, such as dogs and cats; laboratory animals, such as rats, mice and rabbits. In some embodiments, the mammal is a human.

Administration of Prodrug Forms of the Aromatic-Cationic Peptides of the Present Technology The aromatic-cationic peptides of the present technology can be administered in prodrug form. Prodrugs are derivatives of the aromatic-cationic peptides, which are themselves relatively inactive, but which convert into the active compound when introduced into the subject in which they are used, by a chemical or biological process in vivo, such as an enzymatic conversion. Further discussion of suitable prodrugs is provided in H. Bundgaard, *Design of Prodrugs*, New York: Elsevier, 1985; in R. Silverman, *The Organic Chemistry of Drug Design and Drug Action*, Boston: Elsevier, 2004; in R. L. Juliano (ed.), *Biological Approaches to the Controlled Delivery of Drugs* (Annals of the New York Academy of Sciences, v. 507), New York: N.Y. Academy of Sciences, 1987; and in E. B. Roche (ed.), *Design of Biopharmaceutical Properties Through Prodrugs and Analogs* (Symposium sponsored by Medicinal Chemistry Section, APhA Academy of Pharmaceutical Sciences, November 1976 national meeting, Orlando, Fla.), Washington: The Academy, 1977.

Combination Therapy with an Aromatic-Cationic Peptide of the Present Technology and Other Therapeutic Agents In some embodiments, the aromatic-cationic peptides of the present technology may be combined with one or more additional therapeutic agents for the prevention, amelioration, or treatment of vitiligo. For example, the treatment for vitiligo typically involves applying topical steroid creams, monobenzone, or administering psoralen photochemotherapy. In addition, antibiotics, hormones, antineoplastic agents, immunomodulators, dermatologic drugs, antithrombotic and antianemic agents, by way of non-limiting example, may also be administered.

In one embodiment, the aromatic-cationic peptide is combined with one or more therapeutic agents consisting of topical steroids, topical or oral psoralen, monobenzone, or photochemotherapy.

In one embodiment, an additional therapeutic agent is administered to a subject in combination with an aromatic-cationic peptide of the present technology, such that a synergistic therapeutic effect is produced. A "synergistic therapeutic effect" refers to a greater-than-additive therapeutic effect which is produced by a combination of two therapeutic agents, and which exceeds that which would otherwise result from individual administration of either therapeutic agent alone. Therefore, lower doses of one or both of the therapeutic agents may be used in treating vitiligo, resulting in increased therapeutic efficacy and decreased side-effects.

In any case, the multiple therapeutic agents (including, but not limited to, e.g., aromatic-cationic peptide of the present technology) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

Diagnostic Methods Using Aromatic-Cationic Peptides

In some embodiments, at least one aromatic-cationic peptide of the present technology, or pharmaceutically acceptable salt thereof, such as acetate, tartrate salt, or trifluoroacetate salt, is used in a diagnostic assay to determine whether a subject suffering from vitiligo is a candidate to undergo treatment with at least one aromatic-cationic peptide.

In some embodiments, a subject diagnosed with vitiligo is selected as a candidate for treatment with at least one aromatic-cationic peptide (e.g., D-Arg-2',6'-Dmt-Lys-Phe-NH$_2$), or a pharmaceutically acceptable salt thereof, such as acetate, tartrate salt, or trifluoroacetate salt, using one or more of, but not limited to, the following criteria: subject has a confirmed diagnosis of non-segmental vitiligo (NSV) with 15% to 50% of total body surface involvement; NSV involving the head and neck; stable or slowly progressive vitiligo over a 3-month period; the subject is at least 13 years old; and the subject has at least one vitiligo lesion measuring at least 2×2 cm in size. Additionally, or alternatively, in some embodiments, a subject diagnosed with vitiligo is selected as a candidate for treatment with at least one aromatic-cationic peptide if the subject has a family history of vitiligo, the subject suffers from at least one autoimmune disease, or the subject has a variation in one or more genes, wherein the genes include, but are not limited to, NLRP1, TYR, HLA class I, HLA class II, HLA class III, PTPN22, XBP1, IL2RA, LPP, RERE, FOXP1, TSLP, CCR6, GZMB, UBASH3A, C1QTNF6, and FOXP3. By way of example, but not by way of limitation, in some embodiments, the autoimmune disease includes, but is not limited to, Hashimoto's thyroiditis, Graves' disease, pernicious anemia, rheumatoid arthritis, psoriasis, type I diabetes, Addison's disease, celiac disease, inflammatory bowel disorder, and systemic lupus erythematosus.

By way of example, but not by way of limitation, in some embodiments, a diagnostic method for identifying a subject diagnosed with vitiligo suitable for treatment with aromatic-cationic peptides includes any combination of one or more of the following steps: removing tissue from one or more affected skin areas (e.g., an area of skin displaying the phenotype of vitiligo) from a subject diagnosed with vitiligo, isolating the melanocytes and/or keratinocytes of from the tissues, culturing the isolated melanocytes and/or keratinocytes, dividing the melanocytes and/or keratinocytes into two or more groups, treating at least one of the groups of melanocytes and/or keratinocytes with at least one aromatic-cationic peptide (e.g., D-Arg-2',6'-Dmt-Lys-Phe-NH$_2$), treating at least one of the groups of melanocytes and/or keratinocytes with a vehicle control (i.e., no treatment with an aromatic-cationic peptide), assaying the melanocytes and/or keratinocytes for a therapeutic effect, and comparing the therapeutic effects of the at least one aromatic-cationic peptide (e.g., D-Arg-2',6'-Dmt-Lys-Phe-NH$_2$) on treated and untreated melanocytes and/or keratinocytes. In some embodiments, assaying the melanocytes and/or keratinocytes for a therapeutic effect includes, but is not limited to, assaying for one or more of: an increased mitochondrial membrane potential, an increased production of ATP, an increase in cell survival or proliferation, and an increase in melanin production.

In some embodiments, the therapeutic effect of the aromatic-cationic peptide on treated and untreated melanocytes and/or keratinocytes from the subject diagnosed with vitiligo is compared to melanocytes and/or keratinocytes from a subject not diagnosed with vitiligo. In some embodiments, a subject is deemed not to suffer from vitiligo if the subject that does not express the phenotype for vitiligo (e.g., patches of white skin on the face, neck, hands, or knees), does not express a gene variation in one or more of the following genes: NLRP1, TYR, HLA class I, HLA class II, HLA class III, PTPN22, XBP1, IL2RA, LPP, RERE, FOXP1, TSLP, CCR6, GZMB, UBASH3A, C1QTNF6, and FOXP3, does not have an autoimmune disease, or does not have a family history of vitiligo.

In some embodiments, a subject diagnosed with vitiligo is a selected for treatment with at least one aromatic-cationic peptide (e.g., D-Arg-2',6'-Dmt-Lys-Phe-NH$_2$), or a pharmaceutically acceptable salt thereof, if there is an increase of about 1% to 50%, 5% to 40%, 10% to 30%, or 15% to 25% in mitochondrial membrane potential, ATP production, in cell survival, cell proliferation, or melanin production in aromatic-cationic peptide treated melanocytes and/or keratinocytes from the subject diagnosed with vitiligo as compared to untreated melanocytes and/or keratinocytes from the same subject.

Additionally, or alternatively, in some embodiments, a subject diagnosed with vitiligo is selected for treatment with at least one aromatic-cationic peptide (e.g., D-Arg-2',6'-Dmt-Lys-Phe-NH$_2$), or a pharmaceutically acceptable salt thereof, if the mitochondrial membrane potential, ATP production, cell survival, cell proliferation, or melanin production of aromatic-cationic peptide treated melanocytes and/or keratinocytes from the subject diagnosed with vitiligo returns to normal levels by about 1% to 50%, 5% to 40%, 10% to 30%, or 15% to 25%. In some embodiments, normal levels of mitochondrial membrane potential, ATP production, cell survival, cell proliferation, or melanin production are established by assaying melanocytes and/or keratinocytes from one or more subjects not diagnosed with vitiligo. By way of example, but not by way of limitation, in some embodiments, normal levels of mitochondrial membrane potential, ATP production, cell survival, cell proliferation, or melanin production are established by averaging the levels of mitochondrial membrane potential, ATP production, cell survival, cell proliferation, or melanin production from at least three different subjects not diagnosed with vitiligo.

In some embodiments, after a subject diagnosed with vitiligo is receiving treatment with at least one aromatic-cationic peptide of the present technology, or pharmaceutically acceptable salt thereof, such as acetate, tartrate salt, or trifluoroacetate salt, the subject undergoing aromatic-cationic peptide treatment is monitored for one or more therapeutic effects of the aromatic-cationic peptide treatment. By way of example, but not by way of limitation, in some embodiments, monitoring the aromatic-cationic peptide treatment includes any combination of one or more of the following steps: removing a biopsy tissue from one or more affected skin areas of a vitiligo subject undergoing aromatic-cationic treatment, isolating the melanocytes and/or keratinocytes of from the tissues, culturing the isolated melanocytes and/or keratinocytes, assaying the isolated melanocytes and/or keratinocytes for a therapeutic effect by the aromatic-cationic treatment, comparing the therapeutic effects of treatment with aromatic-cationic peptide to a normalized or standardized levels of melanocytes and/or keratinocytes cellular energetics, melanin production, and/or cell proliferation, and comparing the therapeutic effects of treatment with aromatic-cationic peptide to the original levels of melanocyte and/or keratinocytes cellular energetics, melanin production, and/or cell proliferation from the vitiligo subject before treatment with the aromatic-cationic peptide from the vitiligo subject before treatment with the aromatic-cationic peptide. In some embodiments, the therapeutic effect assayed for includes, but is not limited to, one or more of: an increased mitochondrial membrane potential of mitochondria in melanocytes, an increased production of ATP in melanocytes, an increase in cell survival or proliferation of in melanocytes, and an increase in melanin production by the melanocytes.

As used herein, "normalized" or "standardized" levels of cellular energetics, melanin production, and/or cell proliferation refers to normal levels of mitochondrial membrane potential, ATP production, cell survival, cell proliferation, or melanin production melanocytes and/or keratinocytes from a subject not diagnosed with vitiligo. By way of example, but not by way of limitation, in some embodiments, normal levels of mitochondrial membrane potential, ATP production, cell survival, cell proliferation, or melanin production are established by averaging the levels of mitochondrial membrane potential, ATP production, cell survival, cell proliferation, or melanin production from at least three different subjects not diagnosed with vitiligo.

In some embodiments, at least one aromatic-cationic peptide of the present technology, or pharmaceutically acceptable salt thereof, such as acetate, tartrate salt, or trifluoroacetate salt, is used in a screening assay to determine the efficacy of a therapy for vitiligo. In some embodiments, the vitiligo therapy in which the efficacy is to be determined is compared to treatment with at least one aromatic-cationic peptide, or pharmaceutically acceptable salt thereof, such as acetate, tartrate salt, or trifluoroacetate salt.

By way of example, but not by way of limitation, in some embodiments, a screening assay for determining the efficacy of a vitiligo therapy includes any combination of the following: removing tissue from an affected skin area of a subject diagnosed with vitiligo, isolating the melanocytes of from the tissue, culturing the isolated melanocytes, dividing the melanocytes into two or more groups, treating at least one of the groups of melanocytes with D-Arg-2',6'-Dmt-Lys-Phe-NH$_2$, treating at least one of the groups of melanocytes with a vehicle control (i.e., non-treated cells), treating at least one group of melanocytes with the vitiligo therapy (i.e., the vitiligo therapy in which the efficacy is to be determined), assaying the melanocytes for a therapeutic effect by the treatment with D-Arg-2',6'-Dmt-Lys-Phe-NH$_2$ and the vitiligo therapy, and comparing the therapeutic effects of treatment with D-Arg-2',6'-Dmt-Lys-Phe-NH$_2$ to the same therapeutic with treatment with the vitiligo therapy. In some embodiments, the therapeutic effect assayed for includes, but is not limited to, one or more of: an increased mitochondrial membrane potential of mitochondria in melanocytes, an increased production of ATP in melanocytes, an increase in cell survival or proliferation of in melanocytes, and an increase in melanin production by the melanocytes. In some embodiments, a vitiligo therapy is considered effective if the treatment of melanocytes with the vitiligo therapy has a greater or equal therapeutic effect as treatment of melanocyte with D-Arg-2',6'-Dmt-Lys-Phe-NH$_2$.

In another embodiment, a screening assay for determining the efficacy of a vitiligo therapy includes any combination of the following: dividing mice from any vitiligo mouse models known in the art into at least two groups, treating at least one group of mice with the vitiligo therapy (i.e., the vitiligo therapy in which the efficacy is to be determined), treating at least one group of mice with at least one aromatic-cationic peptide, e.g., D-Arg-2',6'-Dmt-Lys-Phe-NH$_2$, treating at least one group of mice with a vehicle control (i.e., non-treated mice), and comparing the therapeutic effects of the vitiligo therapy and aromatic-cationic treatment on the mice. In some embodiments, the therapeutic effects compared include, but are not limited, the decrease of white patches of fur on the mice, an increased mitochondrial membrane potential of mitochondria in the mice's melanocytes, an increased production of ATP in the mice's melanocytes, an increase in cell survival or proliferation of in the mice's melanocytes, and an increase in melanin production by the mice's melanocytes. In some embodiments, a vitiligo therapy is considered effective if the treatment of mice with the vitiligo therapy has a greater or equal therapeutic effect as treatment of mice with D-Arg-2',6'-Dmt-Lys-Phe-NH$_2$.

EXAMPLES

The present technology is further illustrated by the following examples, which should not be construed as limiting in any way. For each of the examples below, any aromatic-cationic peptide described herein could be used. By way of example, but not by limitation, the aromatic-cationic peptide used in the examples below could be 2',6'-Dmt-D-Arg-Phe-Lys-NH$_2$, Phe-D-Arg-Phe-Lys-NH$_2$, or D-Arg-2',6'-Dmt-Lys-Phe-NH$_2$.

Example 1: Treatment of Vitiligo Melanocytes with D-Arg-2',6'-Dmt-Lys-Phe-NH$_2$ This example demonstrates the effect of D-Arg-2',6'-Dmt-Lys-Phe-NH$_2$ on mitochondrial membrane potential and ATP production of melanocytes isolated from subjects diagnosed with vitiligo.

Methods

Mitochondrial Membrane Potential: Melanocytes were isolated and cultured from three human patients that do not have vitiligo (NHM) and from three human patients diagnosed with vitiligo (VHM). Cultured melanocytes from each patient were divided into three groups, wherein each group was treated with D-Arg-2',6'-Dmt-Lys-Phe-NH$_2$ at 0 µM, 1.5 µM, and 2 µM. D-Arg-2',6'-Dmt-Lys-Phe-NH$_2$ added to the growth media each day for 7 days. After 7 days, mitochondrial membrane potential ($\Delta\Psi_m$) of the melanocytes were assessed with a JC-1 probe (see, e.g., JC-1 Mitochondrial Membrane Potential Assay Kit, Cayman Chemical Co., Ann Arbor, Mich.). FIG. 1 shows the average change in mitochondrial membrane potential of the melanocytes from the three NHM cultures and the three VHM cultures.

ATP Production:

Melanocytes were isolated and cultured from two human patients diagnosed with vitiligo (VHM). Cultured melanocytes from each patient were divided into two groups, wherein each group was treated with D-Arg-2',6'-Dmt-Lys-Phe-NH$_2$ at 0 µM and 2 µM. D-Arg-2',6'-Dmt-Lys-Phe-NH$_2$ was added to the growth media each day for 3 days. After 3 days, the melanocytes were lysed and ATP levels were measures by fluorimetric determination. Each assay was performed in triplicate. FIG. 2 shows the average amount of ATP in the melanocytes from the respective treated and untreated groups of the VHM cultures.

Results

FIG. 1 shows that the treatment of VHM melanocytes with D-Arg-2'6'-Dmt-Lys-Phe-NH$_2$ nearly doubled the mitochondrial membrane potential of the VHM melanocytes. Additionally, treatment of VHM melanocytes with D-Arg-2',6'-Dmt-Lys-Phe-NH$_2$ returned the mitochondrial membrane potential of the VHM melanocytes to levels found in untreated NHM melanocytes.

FIG. 2 shows that the treatment of VHM melanocytes with D-Arg-2',6'-Dmt-Lys-Phe-NH$_2$ at 2 µM elevated ATP production levels as compared to untreated VHM melanocytes.

The results show that treatment with D-Arg-2',6'-Dmt-Lys-Phe-NH$_2$ improves the mitochondrial membrane potential and ATP production of VHM melanocytes. As such, treatment of VHM melanocyte with D-Arg-2',6'-Dmt-Lys-Phe-NH$_2$ improves the mitochondrial energetics of VHM melanocytes. Accordingly, aromatic-cationic peptides of the present technology, or a pharmaceutically acceptable salt thereof, such as acetate, tartrate salt, or trifluoroacetate salt, including but not limited to D-Arg-2',6'-Dmt-Lys-Phe-NH$_2$, are useful in improving the cellular dynamics and/or normalizing the mitochondrial membrane potential and ATP production of melanocytes in a subject suffering from or predisposed to vitiligo.

Example 2: Therapeutic Effect of D-Arg-2',6'-Dmt-Lys-Phe-NH$_2$ on 4-TBP-Induced Cytotoxicity and Apoptosis in Melanocytes This example will demonstrate the therapeutic effect of D-Arg-2',6'-Dmt-Lys-Phe-NH$_2$ on 4-TBP-induced vitiligo.

Melanocytes are cultured and treated with 4-TBP to induce vitiligo according to the procedures described in Yang & Boissy, *Pigment Cell Research*, 12:237-245 (1999). The experimental group of melanocytes is treated with 1-10 μg of D-Arg-2',6'-Dmt-Lys-Phe-NH$_2$ after exposure to 4-TBP. The control melanocyte group is exposed to 4-TBP only.

Results

It is anticipated that untreated melanocytes will exhibit high levels of cytotoxicity and apoptosis following exposure to 4-TBP (Vitiligo control) compared to melanocytes that are not exposed to 4-TBP (Normal). However, it is anticipated that melanocytes treated with D-Arg-2',6'-Dmt-Lys-Phe-NH$_2$ will show cell survival rates that are similar to normal melanocytes that are not exposed to 4-TBP and greater than untreated melanocytes following 4-TBP exposure.

These results will show that aromatic-cationic peptides of the present technology, or pharmaceutically acceptable salts thereof, such as acetate salts, tartrate salts, or trifluoroacetate salts, are useful in treating apoptosis and cytotoxicity associated with chemically-induced vitiligo. Accordingly, the aromatic-cationic peptides of the present technology, or a pharmaceutically acceptable salt thereof, such as acetate, tartrate salt, or trifluoroacetate salt, including but not limited to D-Arg-2,'6'-Dmt-Lys-Phe-NH$_2$, are useful in treating, preventing, or ameliorating melanocyte degeneration and depigmentation observed in a subject suffering from or predisposed to vitiligo.

Example 3: Prophylactic Effect of D-Arg-2',6'-Dmt-Lys-Phe-NH$_2$ on 4-TBP-Induced Cytotoxicity and Apoptosis in Melanocytes This example will demonstrate the prophylactic effect of D-Arg-2',6'-Dmt-Lys-Phe-NH$_2$ on 4-TBP-induced vitiligo.

Melanocytes are cultured with 1-10 μg of D-Arg-2',6'-Dmt-Lys-Phe-NH$_2$ for one week. A control group of melanocytes is cultured in parallel without the aromatic-cationic peptide. Both the experimental and the control groups are subsequently treated with 4-TBP to induce vitiligo according to the procedures described in Yang & Boissy, *Pigment Cell Research*, 12:237-245 (1999).

Results

It is anticipated that melanocytes within the control group will exhibit high levels of cytotoxicity and apoptosis following exposure to 4-TBP compared to melanocytes that are not exposed to 4-TBP (Normal). However, it is anticipated that melanocytes that are cultured with D-Arg-2',6'-Dmt-Lys-Phe-NH$_2$ prior to contact with 4-TBP will show cell survival rates that are similar to normal melanocytes that are not exposed to 4-TBP and greater than untreated melanocytes following 4-TBP exposure.

These results will show that aromatic-cationic peptides of the present technology, or pharmaceutically acceptable salts thereof, such as acetate salts, tartrate salt, or trifluoroacetate salts, are useful in preventing apoptosis and cytotoxicity associated with chemically-induced vitiligo. Accordingly, the aromatic-cationic peptides of the present technology, or a pharmaceutically acceptable salt thereof, such as acetate, tartrate salt, or trifluoroacetate salt, including but not limited to D-Arg-2',6'-Dmt-Lys-Phe-NH$_2$, are useful in treating, preventing, or ameliorating melanocyte degeneration and depigmentation observed in a subject suffering from or predisposed to vitiligo.

Example 4: Effect of D-Arg-2',6'-Dmt-Lys-Phe-NH$_2$ on T-Cell Accumulation and Cytotoxic Activity in Autologous Vitiligo Skin Explants This example will demonstrate the effect of D-Arg-2',6'-Dmt-Lys-Phe-NH$_2$ on T-cell accumulation and cytotoxic activity in a vitiligo skin explant model.

Active vitiligo patients are subdivided into 2 groups. Group I subjects are administered a daily dose of 0.25 mg/kg/day of D-Arg-2',6'-Dmt-Lys-Phe-NH$_2$ for twelve weeks whereas Group II vitiligo subjects are treated with drug vehicle and serve as controls. Punch-biopsies are obtained flanking the depigmented macule from Group I and Group II vitiligo subjects. These biopsies are cultured to promote T-cell growth according to the procedures described in Van Den Boom et al., *Journal of Investigative Dermatology*, 129: 2220-2232 (2009). The ability of these perilesional T-cells to infiltrate and actively kill melanocytes within the skin tissue microenvironment is tested using skin explant assays. Autologous skin explants are generated according to the procedures described in Van Den Boom et al., *Journal of Investigative Dermatology*, 129: 2220-2232 (2009). Perilesional T-cells are co-cultured with normally pigmented autologous skin explants for 2 days. T-cells are allowed to infiltrate the skin explants and migrate toward the melanocytes located at the dermal-epidermal junction. Skin explant cryosections are analyzed for the presence of infiltrated T-cells, melanocytes, and apoptosis by immunohistochemistry or immunofluorescence as described in Van Den Boom et al., *Journal of Investigative Dermatology*, 129: 2220-2232 (2009).

Results

It is anticipated that autologous skin explants from untreated vitiligo subjects will exhibit high levels of T-cell accumulation and melanocyte destruction compared to skin explants retrieved from normal subjects. It is further anticipated that skin explants from subjects treated with D-Arg-2',6'-Dmt-Lys-Phe-NH$_2$ will show T-cell accumulation and melanocyte survival rates that are similar to skin explants retrieved from normal subjects. It is further anticipated that skin explants from subjects treated with D-Arg-2',6'-Dmt-Lys-Phe-NH$_2$ will show melanocyte survival rates that are greater than untreated vitiligo explants.

These results will show that aromatic-cationic peptides of the present technology, or pharmaceutically acceptable salts thereof, such as acetate salts, tartrate salt, or trifluoroacetate salts, are useful in suppressing T-cell accumulation and cytotoxic activity in a vitiligo skin explant model. Accordingly, the aromatic-cationic peptides of the present technology, or a pharmaceutically acceptable salt thereof, such as acetate, tartrate salt, or trifluoroacetate salt, including but not limited to D-Arg-2',6'-Dmt-Lys-Phe-NH$_2$, are useful in treating, preventing, or ameliorating melanocyte degeneration and depigmentation observed in a subject suffering from or predisposed to vitiligo.

Example 5: Effect of D-Arg-2'6'-Dmt-Lys-Phe-NH$_2$ on Progressive Depigmentation in the Pelage of the Vitiligo Mouse Model This example will demonstrate the effect of D-Arg-2',6'-Dmt-Lys-Phe-NH$_2$ on progressive depigmentation in the pelage of the vitiligo mouse model.

Vitiligo mice described in Lerner et al., *Journal of Investigative Dermatology*, 87: 299-304 (1986) are obtained. Vitiligo mice are subdivided into 2 groups. Group I mice are administered a daily dose of 0.25 mg/kg/day of D-Arg-2',6'-Dmt-Lys-Phe-NH$_2$ for four weeks before plucking dorsal hairs whereas Group II vitiligo mice are treated with drug vehicle before plucking. The regrowth of amelanotic hairs is monitored via light microscopy.

Results

It is anticipated that untreated vitiligo mice will show progressive replacement of pigmented hairs by white hairs after plucking. It is further anticipated that vitiligo mice treated with D-Arg-2',6'-Dmt-Lys-Phe-NH$_2$ will show a reduced rate of progressive depigmentation 2 weeks after plucking dorsal hairs compared to untreated vitiligo mice.

These results will show that aromatic-cationic peptides of the present technology, or pharmaceutically acceptable salts thereof, such as acetate salts, tartrate salts, or trifluoroacetate salts, are useful in delaying or ameliorating the rate of progressive depigmentation in the pelage of the vitiligo mouse model relative to untreated vitiligo controls. Accordingly, the aromatic-cationic peptides of the present technology, or a pharmaceutically acceptable salt thereof, such as acetate, tartrate salt, or trifluoroacetate salt, including but not limited to D-Arg-2',6'-Dmt-Lys-Phe-NH$_2$, are useful in treating, preventing, or ameliorating melanocyte degeneration and depigmentation observed in a subject suffering from or predisposed to vitiligo.

Example 6: Effect of D-Arg-2' 6'-Dmt-Lys-Phe-NH$_2$ on Epidermal Depigmentation in an Adoptive Transfer Mouse Model of Vitiligo Vitiligo mice described in Harris et al., *Journal of Investigative Dermatology*, 132: 1869-1876 (2012) are obtained. This adoptive transfer mouse model of vitiligo recapitulates the human condition by inducing epidermal depigmentation while sparing the hair. These mice are subdivided into 2 groups. Group I mice are administered a daily dose of 0.25 mg/kg/day of D-Arg-2',6'-Dmt-Lys-Phe-NH$_2$ for four weeks whereas Group II vitiligo mice are treated with drug vehicle and serve as controls. The loss of pigmentation in epidermal tissues such as the tail, nose and footpad is monitored via light microscopy.

Results

It is anticipated that these untreated vitiligo mice will show progressive loss of pigmentation in epidermal tissues such as the tail, nose and footpad. It is further anticipated that vitiligo mice treated with D-Arg-2',6'-Dmt-Lys-Phe-NH$_2$ will show a reduced severity of depigmentation in epidermal tissues compared to untreated vitiligo mice.

These results will show that aromatic-cationic peptides of the present technology, or pharmaceutically acceptable salts thereof, such as acetate salts, tartrate salt, or trifluoroacetate salts, are useful in reducing the rate of depigmentation in the epidermal tissues in an adoptive transfer mouse model of vitiligo. Accordingly, the aromatic-cationic peptides of the present technology, or a pharmaceutically acceptable salt thereof, such as acetate, tartrate salt, or trifluoroacetate salt, including but not limited to D-Arg-2',6'-Dmt-Lys-Phe-NH$_2$, are useful in treating, preventing, or ameliorating melanocyte degeneration and depigmentation observed in a subject suffering from or predisposed to vitiligo.

EQUIVALENTS

The present technology is not to be limited in terms of the particular embodiments described in this application, which are intended as single illustrations of individual aspects of the present technology. Many modifications and variations of this present technology can be made without departing from its spirit and scope, as were apparent to those skilled in the art. Functionally equivalent methods and apparatuses within the scope of the present technology, in addition to those enumerated herein, were apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As were understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as were understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method for treating vitiligo in a subject in need thereof, the method comprising: administering a therapeutically effective amount of the peptide D-Arg-2',6'-Dmt-Lys-Phe-NH$_2$ or a pharmaceutically acceptable salt thereof.

2. The method of claim 1, wherein the symptoms of vitiligo are selected from the group consisting of increased photosensitivity, decreased contact sensitivity response to dimtrochlorobenzene, depigmentation of the skin, mucous membranes, retina, or genitals, and premature whitening or graying of hair on the scalp, eyelashes, eyebrows or beard.

3. The method of claim 1, wherein vitiligo is associated with one or more of the following: autoimmune thyroid disease, pernicious anemia, rheumatoid arthritis, psoriasis, type I diabetes, Addison's disease, celiac disease, inflammatory bowel disorder, and systemic lupus erythematosus.

4. The method of claim 1, wherein vitiligo is associated with at least one gene mutation located in the group consisting of NLRP1, TYR, HLA class I, HLA class II, HLA class III, PTPN22, XBP1, IL2RA, LPP, RERE, FOXP1, TSLP, CCR6, GZMB, UBASH3A, C1QTNF6, and FOXP3.

5. The method of claim 1, wherein the peptide is administered orally, topically, systematically, intravenously, subcutaneously, intraperitoneally, or intramuscularly.

6. The method of claim 1, further comprising sequentially, separately, or simultaneously administering one or more therapeutic agents selected from the group consisting of: topical steroid creams, monobenzone, psoralen photochemotherapy, antibiotics, hormones, antineoplastic agents, immunomodulators, dermatologic drugs, antithrombotic agents, and antianemic agents.

7. The method of claim 2, wherein the mucous membranes comprise tissues lining the inside of the mouth and nose.

8. The method of claim 3, wherein the autoimmune thyroid disease is Hashimoto's thyroiditis or Graves' disease.

* * * * *